United States Patent
Ryan et al.

(10) Patent No.: US 9,120,854 B2
(45) Date of Patent: Sep. 1, 2015

(54) DETECTION AND TREATMENT OF PANCREATIC, OVARIAN AND OTHER CANCERS

(75) Inventors: Maureen Ryan, Bellevue, WA (US); Maria Leia Smith, Seattle, WA (US)

(73) Assignee: SEATTLE GENETICS, INC., Bothell, WA (US)

( * ) Notice: Subject to any disclaimer, the term of this patent is extended or adjusted under 35 U.S.C. 154(b) by 172 days.

(21) Appl. No.: 12/937,190

(22) PCT Filed: Apr. 10, 2009

(86) PCT No.: PCT/US2009/040275
§ 371 (c)(1),
(2), (4) Date: Oct. 8, 2010

(87) PCT Pub. No.: WO2009/126934
PCT Pub. Date: Oct. 15, 2009

(65) Prior Publication Data
US 2011/0300131 A1 Dec. 8, 2011

Related U.S. Application Data

(60) Provisional application No. 61/044,457, filed on Apr. 11, 2008.

(51) Int. Cl.
G01N 33/567 (2006.01)
C07K 16/18 (2006.01)
C07K 16/28 (2006.01)
G01N 33/566 (2006.01)
G01N 33/53 (2006.01)
G01N 33/574 (2006.01)
C07K 14/705 (2006.01)

(52) U.S. Cl.
CPC ............ *C07K 16/2875* (2013.01); *C07K 16/18* (2013.01); *G01N 33/53* (2013.01); *G01N 33/566* (2013.01); *G01N 33/574* (2013.01); *G01N 33/57407* (2013.01); *C07K 14/70575* (2013.01); *C07K 2317/56* (2013.01); *C07K 2317/565* (2013.01); *C07K 2319/01* (2013.01); *G01N 2333/70575* (2013.01)

(58) Field of Classification Search
CPC ............... C07K 16/18; C07K 16/2875; C07K 14/70575; G01N 33/53; G01N 33/566; G01N 33/574
USPC ........... 530/350, 387.1, 387.3, 387.7, 388.22, 530/388.23, 388.8, 388.2; 435/7.1, 7.21, 435/7.23
See application file for complete search history.

(56) References Cited

U.S. PATENT DOCUMENTS

| | | |
|---|---|---|
| 7,261,892 B2 | 8/2007 | Terrett |
| 7,491,390 B2 | 2/2009 | Law et al. |
| 7,641,903 B2 | 1/2010 | Law et al. |
| 7,662,387 B2 | 2/2010 | Law et al. |
| 7,745,156 B2 | 6/2010 | Terrett et al. |
| 8,067,546 B2 | 11/2011 | Law et al. |
| 2005/0118656 A1 | 6/2005 | Terrett |
| 2005/0123547 A1 | 6/2005 | Terrett |
| 2005/0191299 A1 | 9/2005 | Swamy et al. |
| 2006/0083736 A1 | 4/2006 | Law et al. |
| 2006/0233794 A1 | 10/2006 | Law et al. |
| 2007/0292422 A1 | 12/2007 | Law et al. |
| 2008/0025989 A1 | 1/2008 | Law et al. |
| 2008/0138341 A1 | 6/2008 | Law et al. |
| 2008/0138343 A1 | 6/2008 | Law et al. |
| 2009/0074772 A1 | 3/2009 | Law et al. |
| 2009/0148439 A1 | 6/2009 | Terrett |
| 2009/0148942 A1 | 6/2009 | Law et al. |
| 2009/0232806 A1 | 9/2009 | Law et al. |
| 2010/0015665 A1 | 1/2010 | Latham et al. |
| 2010/0036091 A1 | 2/2010 | Robinson et al. |
| 2010/0129362 A1 | 5/2010 | Law et al. |
| 2010/0150925 A1 | 6/2010 | Law et al. |
| 2010/0150950 A1 | 6/2010 | Coccia et al. |
| 2010/0158910 A1 | 6/2010 | Law et al. |
| 2010/0183636 A1 | 7/2010 | Law et al. |
| 2011/0150908 A1 | 6/2011 | Law et al. |
| 2012/0045436 A1 | 2/2012 | Law et al. |

FOREIGN PATENT DOCUMENTS

| | | |
|---|---|---|
| WO | WO 01/94629 | 12/2001 |
| WO | WO 03/046581 | 6/2003 |
| WO | WO 2004/010957 | 2/2004 |
| WO | WO 2004/073656 | 9/2004 |
| WO | WO 2006/044643 | 4/2006 |
| WO | WO 2006/113909 | 10/2006 |
| WO | WO 2007/038637 | 4/2007 |
| WO | WO 2008/074004 | 6/2008 |

OTHER PUBLICATIONS

Sloan et al. (Am. J. Pathol. Jan. 2004; 164 (1): 315-23).*
Junker et al. (J. Urol. Jun. 2005; 173 (6): 2150-3).*
Chahlavi et al. (Cancer Res. Jun. 15, 2005; 65 (12): 5428-38).*
Balyasnikova et al. (Tissue Antigens. Jan. 2003; 61 (1): 49-62).*
George et al. (Circulation. 1998; 97: 900-906).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*

(Continued)

*Primary Examiner* — Stephen Rawlings
(74) *Attorney, Agent, or Firm* — Seattle Genetics, Inc.

(57) ABSTRACT

The application provides methods of diagnosis, prognosis, prophylaxis and treatment of ovarian, pancreatic and other cancers using antibodies that specifically bind to denatured CD70.

9 Claims, 11 Drawing Sheets

(56) References Cited

OTHER PUBLICATIONS

MacCallum et al. (J. Mol. Biol. Oct. 11, 1996; 262 (5): 732-745).*
Holm et al. (Mol. Immunol. Feb. 2007; 44 (6): 1075-1084).*
Winkler et al. (J. Immunol. Oct. 15, 2000; 165 (8): 4505-4514).*
Moran et al. (J. Immunol. Methods. Oct. 1, 1998; 219 (1-2): 151-9).*
Balyasnikova et al. (Tissue Antigens. Mar. 2005; 65 (3): 240-51).*
Held-Feindt et al. (Int. J. Cancer. Mar. 20, 2002; 98 (3): 352-6).*
Uejima et al. (Cancer Res. Nov. 15, 1992; 52 (22): 6158-63).*
Li et al. (Biochem. Biophys. Res. Commun. Sep. 18, 1998; 250 (2): 502-5).*
Prud'homme et al. (Cancer Res. Apr. 15, 1990; 50 (8): 2390-6).*
Abcam® PLC product datasheet "ab77868" (accessed from the Internet and printed Oct. 27, 2014).*
Hoyer-Hansen et al. (J. Immunol. Methods. Feb. 21, 2000; 235 (1-2): 91-9).*
Ito et al. (J. Immunol. Aug. 1, 1999; 163 (3): 1409-19).*
Liu et al. (Onco. Targets Ther. Jun. 5, 2013; 6: 615-9).*
LifeSpan Biosciences, Inc. Product Datasheet "LS-A8809" (accessed from the Internet; printed Oct. 27, 2014).*
Abcam® PLC Product Datasheet "ab133398" (accessed from the Internet and printed Oct. 27, 2014).*
Abcam® PLC Product Datasheet "ab175389" (accessed from the Internet and printed Oct. 27, 2014).*
Stam et al. (Int. Immunol. 1990; 2 (2): 113-25).*
Adam, et al. "CD70 (TNFSF7) is expressed at high prevalence in renal cell carcinomas and is rapidly internalised on antibody binding" British J. of Cancer. 95:298-306 (2006).
Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells," Am. J. Pathol., 1995; 147(4):1152-1160.
Agematsu et al., "Generation of plasma cells from peripheral blood memory B cells: synergistic effect of interleukin-10 and CD27/CD70 interaction," Blood, 1998; 91(1):173-180.
Agematsu et al., "B cell subpopulations separated by CD27 and crucial collaboration of CD27+ B cells and helper T cells in immunoglobulin production," Eur. J. Immunol., 1997; 27(8):2073-2079.
Aggarwal et al., "Membrane proteomic analyses of ovarian cancer identifies the immune modulators CD70 and B7-H2 as candidate markers of cisplatin response," Abstract No. 2430; 99th AACR Annual Meeting, Apr. 12-16, 2008; San Diego, CA.
Akiba et al., "Critical contribution of OX40 ligand to T helper cell type 2 differentiation in experimental leishmaniasis," J. Exp. Med., 2000; 191(2):375-380.
Baert et al., "Influence of immunogenicity on the long-term effcacy of Infliximab in Crohn's Disease," N. Engl. J. Med., 2003; 348(7):601-608.
Bahler et al., "Clonal evolution of a follicular lymphoma: evidence for antigen selection," Proc. Natl. Acad. Sci. USA, 1992; 89(15):6770-6774.
Bahler et al., "Antigen selection in human lymphomagenesis," Cancer Res. (Suppl.), 1992; 52(19):5547s-5551s.
Bowman et al., "The cloning of CD70 and its identification as the ligand for CD27," J. Immunol., 1994; 152 (4):1756-1761.
Brugnoni et al., "CD70 expression on T-cell subpopulations: study of normal individuals and patients with chronic immune activation," Immunol. Lett., 1997; 55(2):99-104.
Carter, P., "Improving the Effcacy of Antibody-Based Cancer Therapies," Nat Rev Cancer. 2001; 1(2):118-29.
De Jong et al., "Regulation of expression of CD27, a T cell-specific member of a novel family of membrane receptors," J. Immunol., 1991; 146(8):2488-2494.
Dillman, R.O., "Monoclonal antibodies for treating cancer," Ann. Int. Med., 1989; 111:592-603.
Goodwin et al., "Molecular and biological characterization of a ligand for CD27 defines new family of cytokines with homology to tumor necrosis factor," Cell, 1993; 73(3):447-56.
Held-Feindt et al., "CD70/CD27 ligand, a member of the TNF family, is expressed in human brain tumors," Int. J. Cancer, 2002; 98(3):352-356.
Hintzen et al., "Engagement of CD27 with its Ligand CD70 provides a second signal for T cell activation," J. Immunol., 1995; 154(6): 2612-2623.
Hintzen et al., "CD70 represents the human ligand for CD27," Int. Immunol., 1994; 6(3):477-480.
Hintzen et al., "Characterization of the human CD27 Ligand, a novel member of the TNF gene gamily," J. Immunol., 1994; 152(4):1762-1773.
Hintzen et al., "Regulation of CD27 expression on subsets of mature T-lymphocytes," Immunol., 1993; 151 (5):2426-2435.
Hishima et al., "CD70 expression in thymic carcinoma," Am. J. Surg. Pathol., 2000; 24(5):742-746.
Israel et al., "Anti-CD70 antibodies: a potential treatment for EBV+ CD70-expressing lymphomas," Mol. Cancer Ther., 2005; 4(12)2037-44.
Jacquot et al., "CD154/CD40 and CD70/CD27 interactions have different and sequential functions in T cell-dependent B cell responses: enhancement of plasma cell differentiation by CD27 signaling," J. Immunol., 1997; 159 (6):2652-2657.
Kobata et al., "CD27-CD70 interactions regulate B-cell activation by T cells," Proc. Natl. Acad. Sci. USA, 1995; 92 (24):11249-11253.
Law et al., "Lymphocyte activation antigen CD70 expressed by renal cell carcinoma is a potential therapeutic target for anti-CD70 antibody-drug conjugates," Cancer Res., 2006; 66:(4)2328-2337.
Lens et al., "Aberrant expression and reverse signaling of CD70 on malignant B cells," Br. J. Haematol., 1999; 106 (2):491-503.
Lens et al., "Control of lymphocyte function through CD27-CD70 interactions," Semin. Immunol., 1998; 10(6):491-499.
Lens et al., "Antigen-presenting cell-derived signals determine expression levels of CD70 on primed T cells," Immunol., 1997; 90:38-45.
Lens et al., "Phenotype and function of human B cells expressing CD70 (CD27 ligand)," Eur. J. Immunol., 1996; 26 (12):2964-2971.
Locksley et al., "The TNF and TNF receptor superfamilies: integrating mammalian biology," Cell, 2001; 104 (4):487-501.
MacCallum, et al., "Antibody-antigen interactions: contact analysis and binding site topography," J. Mol. Biol., 1996; 262:732-745.
Maurer et al., "CD27 expression by a distinct subpopulation of human B lymphocytes," Eur. J. Immunol., 1990; 20 (12):2679-2684.
McEarchern et al., "Engineered anti-CD70 antibody with multiple effector functions exhibits in vitro and in vivo antitumor activities," Blood, 2007; 109(3)1185-1192.
McEarchern et al., "Engineered Anti-CD70 Antibody Variants Support Multiple Effector Functions and Exhibit Potent In Vitro and In Vivo Antitumor Activities," (abstract) Proc Amer Assoc Cancer Res. 46:6142 (2005).
Nakajima et al., "Involvement of CD70-CD27 interactions in the induction of experimental autoimmune encephalomyelitis," J. Neuroimmunol., 2000; 109(2):188-196.
Oelke et al., "Overexpression of CD70 and overstimulation of IgG synthesis by Lupus T cells and T cells treated with DNA methylation inhibitors," Arthritis Rheum. 2004, 50(6):1850-60.
Oflazoglu et al., "Potent anticarcinoma activity of the humanized anti-CD70 antibody h1F6 conjugated to the tubulin inhibitor auristatin via an uncleavable linker," Clin. Cancer Res. 2008; 14(19):6171-6180.
Orengo et al., "Reciprocal expression of CD70 and of its receptor, CD27, in human long term-activated T and natural kiler (NK) cells: inverse regulation by cytokines and role in induction of cytotoxicity," Clin. Exp. Immunol., 1997; 107(3):608-613.
Oshima et al., "Characterization of murine CD70 by molecular cloning and mAb," Int. Immunol., 1998; 10(4):517-526.
Rannheim et al., "Expression of CD27 and its ligand, CD70, on chronic lymphocytic leukemia B cells," Blood, 1995; 85(12):3556-3565.
Ryan et al., "Targeting pancreatic and ovarian carcinomas using th auristatin-based anti-CD70 antibody-drug conjugate SGN-75," Br, J, Cancer. 2010; 103(5):676-84. Epub Jul. 27, 2010.

(56) References Cited

OTHER PUBLICATIONS

Terrett et al., "CD70 antibody based drugs: two different mechanisms of action for the treatment of multiple cancer types," Proc Amer Assoc Cancer Res, 2006; vol. 47, Abstract #1995.
Wischhusen et al., "Identification of CD70-mediated apoptosis of immune effector cells as a novel immune escape pathway of human glioblastoma," Cancer Res., 2002; 62:2592-2599.
Witzig et al., "Radioimmunotherapy for patients with relapsed B-cell non-Hodgkin lymphoma," Cancer Chemother. Pharmacol., 2001; 48(suppl. 1):S91-S95.
Diegmann et al., "Identification of CD70 as a diagnostic biomarker for clear cell renal cell carcinoma by gene expression profiling, real-time RT-PCR and immunohistochemistry," European J. of Cancer 41:1794-1801, 2005.
Grewal, "CD70 as a therapeutic target in human malignancies," Expert Opin. Ther. Targets 12(3):341-351, 2008.
Junker et al., "CD70: A New Tumor Specific Biomarker for Renal Cell Carcinoma," J. of Urology 173:2150-2153, 2005.
Gordon et al,, "Humanized Anti-CD70 Auristatin Antibody-Drug Conjugates Show Potent In Vitro Cytotoxicity in Renal Cell Carcinoma Primary Cultures Established from Patient Tumor Isolates," Abstract No. 3733, 97th Annual Meeting of the American Association for Cancer Research Apr. 1-5, 2006, Washington, D.C.
Law et al., "Anti-CD70 Auristatin Conjugates with Potent and Selective Activity Against Renal Cell Carcinoma," poster presentation, 4th International Kidney Cancer Symposium, Oct. 21-23, 2005, Chicago, IL.
Law et al., "Anti-CD70 AntibodyDrug Conjugates Mediate Renal Carcinoma Cell Killing Through Cytotoxic Drug Delivery and Antibody-Dependent Cellular Cytotoxicity". (abstract) Proc Amer Assoc Cancer Res. 46:6143 (2005).
McEarchern et al., "A Humanized, Anti-CD70 Monoclonal Antibody Targets CD70 Expressing Multiple Myeloma," Publication No. 1591, 47th Annual Meeting and Exposition of the American Society of Hematology, Dec. 10-13, 2005, Atlanta, GA.
McEarchern, J., "Antitumor Activities of Engineered Anti-CD70 Antibody (h1 F6)", Slides from Oral Presentation by Seattle Genetics at Annual Meeting of American Association for Cancer Research Apr. 16-20:1-15 (2005).
Oflazoglu et al."In Vivo Characterization of the Mechanism of Action of c1F6, an Anti-CD70 Antibody," Abstract No. 3732, 97th Annual Meeting of the American Association for Cancer Research, Apr. 1-5, 2006, Washington, D.C.
Stein et al., "A5 Cluster Report:CDw70," in Leucocyte Typing IV: White Cell Differentiation Antigens, pp. 446-449; Knapp et al., eds., Oxford University Press, 1989.
Terrett et al., "CD70 antibody based drugs: two different mechanisms of action for the treatment of multiple cancer types," Poster Presentation at the 97th Annual Meeting of the American Association for Cancer Research, Apr. 2-5, 2006, Washington, D.C.
CD70 Rabbit anti-Human Polyclonal (Internal)Antibody—LS-A8809—LSBio; www.lsbio.com/antibodies/anti-cd70-antibody-LS-a8809/116828, Aug. 27, 2013.
CD70 Rabbit anti-Human Polyclonal (N-Terminus) Antibody—LS-A8812—LSBio, www.lsbio.com/antibodies/anti-cd70-antibody-LS-a8812/116828, Aug. 27, 2013.
CD70 Rabbit anti-Human Polyclonal (Internal) Antibody—LS-A8811—LSBio, www.lsbio.com/antibodies/anti-cd70-antibody-LS-a8811/116828, Aug. 27, 2013.
Kunder et al. A comprehensive antibody panel for immunohistochemical analysis of formalin-fixed, paraffin-embedded hematopoietic neoplasms of mice: Analysis of mouse specific and human antibodies cross•reactive with murine tissue. Toxicologic Pathology 35:366-375 (2007).
Wang et al. A method to generate antigen-specific mAb capable of staining formalin-fixed, paraffin-embedded tissue sections. Journal of Immunological Methods 299:139-151 (2005).
Anonymous, anti-CD79acy, Clone: HM57, Dako(TM—Fisher Scientific. pp. 1-1, Jan. 1, 2014. XP055100535.

\* cited by examiner

C.

SEQUENCE LISTING

```
<160> NUMBER OF SEQ ID NOS: 4

<210> SEQ ID NO 1
<211> LENGTH: 137
<212> TYPE: PRT
```

<213> ORGANISM: Mus musculus

<400> SEQUENCE: 1

Met Ala Trp Val Trp Thr Leu Leu Phe Leu Met Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Tyr Gly Asp Tyr Gly Met Asp Tyr Trp Gly
        115                 120                 125

Gln Gly Thr Ser Val Thr Val Ser Ser
    130                 135

<210> SEQ ID NO 2
<211> LENGTH: 132
<212> TYPE: PRT
<213> ORGANISM: Mus musculus

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Val Pro Trp Thr Phe Gly Gly Gly Thr Lys Leu
        115                 120                 125

Glu Ile Lys Arg
    130

<210> SEQ ID NO 3
<211> LENGTH: 137
<212> TYPE: PRT
<213> ORGANISM: Mus musculus

<400> SEQUENCE: 3

Met Glu Trp Thr Trp Val Phe Leu Phe Leu Leu Ser Val Thr Ala Asp
1               5                   10                  15

Val Gln Ser Gln Val Gln Leu Gln Gln Ser Gly Thr Glu Leu Met Thr
            20                  25                  30

-continued

```
Pro Gly Ala Ser Val Thr Met Ser Cys Lys Thr Ser Gly Tyr Thr Phe
            35                  40                  45

Ser Thr Tyr Trp Ile Glu Trp Val Lys Gln Arg Pro Gly His Gly Leu
    50                  55                  60

Glu Trp Ile Gly Glu Ile Leu Gly Pro Ser Gly Tyr Thr Asp Tyr Asn
65                  70                  75                  80

Glu Lys Phe Lys Ala Lys Ala Thr Phe Thr Ala Asp Thr Ser Ser Asn
                85                  90                  95

Thr Ala Tyr Met Gln Leu Ser Ser Leu Ala Ser Glu Asp Ser Ala Val
                100                 105                 110

Tyr Tyr Cys Ala Arg Trp Asp Arg Leu Tyr Ala Met Asp Tyr Trp Gly
            115                 120                 125

Gly Gly Thr Ser Val Thr Val Ser Ser
        130                 135

<210> SEQ ID NO 4
<211> LENGTH: 132
<212> TYPE: PRT
<213> ORGANISM: Mus musculus

<400> SEQUENCE: 4

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
                20                  25                  30

Val Ser Leu Gly Gln Lys Thr Thr Ile Ser Cys Arg Ala Ser Lys Ser
            35                  40                  45

Val Ser Thr Ser Gly Tyr Ser Phe Met His Trp Tyr Gln Leu Lys Pro
    50                  55                  60

Gly Gln Ser Pro Lys Leu Leu Ile Tyr Leu Ala Ser Asp Leu Pro Ser
65                  70                  75                  80

Gly Val Pro Ala Arg Phe Ser Gly Ser Gly Ser Gly Thr Asp Phe Thr
                85                  90                  95

Leu Lys Ile His Pro Val Glu Glu Glu Asp Ala Ala Thr Tyr Tyr Cys
                100                 105                 110

Gln His Ser Arg Glu Ile Pro Tyr Thr Phe Gly Gly Gly Thr Lys Leu
            115                 120                 125

Glu Ile Thr Arg
        130
```

DETECTION AND TREATMENT OF PANCREATIC, OVARIAN AND OTHER CANCERS

CONTINUITY

This application is the national stage filing under 35 U.S.C. §371 of International Application No. PCT/US2009/040275 filed Apr. 10, 2009, which published Oct. 15, 2009 as WO2009/126934A2 and which claims the benefit of U.S. Provisional Application No. 61/044,457, filed Apr. 11, 2008, the disclosure of which is incorporated by reference herein in its entirety.

BACKGROUND

CD70 is member of the tumor necrosis factor (TNF) family of cell membrane-bound and secreted molecules that are expressed by a variety of normal and malignant cell types. CD70 is a transmembrane type II protein with its carboxyl terminus exposed to the outside of cells and its amino terminus found in the cytosolic side of the plasma membrane (Bowman et al., 1994, *J. Immunol.* 152:1756-61; Goodwin et al., 1993, *Cell* 73:447-56). Human CD70 contains a 20 amino acid cytoplasmic domain, an 18 AA transmembrane domain, and a 155 AA extracellular domain with two potential N-linked glycosylation sites (Bowman et al., supra; Goodwin et al., supra). Specific immunoprecipitation of radioisotope-labeled CD70-expressing cells by anti-CD70 antibodies yields polypeptides of 29 and 50 kDa (Goodwin et al., supra; Hintzen et al., 1994, *J. Immunol.* 152:1762-73). Based on its homology to TNF-alpha and TNF-beta, a trimeric structure is predicted for CD70 (Petsch et al., 1995, *Mol. Immunol.* 32:761-72).

CD70 has limited expression on normal tissues in humans. This makes CD70 an attractive target for cancer therapies. CD70 expression has been identified, however, on only a small number of cancers, such as renal cell carcinoma, colon cancer, certain types of Non-Hodgkin lymphoma and multiple myeloma. CD70 expression on cancer cells is typically detected using antibodies that bind to native CD70, such as by immunohistochemistry. Detection of CD70 expression on fixed patient samples has proved problematic, due to poor quality antibodies that lack sufficient specificity for CD70. In particular, cross-reactivity and background staining interfere with detection of CD70 in fixed samples. The present invention solves this and other needs.

BRIEF SUMMARY

The invention provides methods of diagnosis, prognosis, prophylaxis and treatment and monitoring treatment of ovarian, pancreatic and other cancers using antibodies to CD70. The invention further provides methods of diagnosis, prognosis, prophylaxis and treatment and monitoring treatment of lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal and bladder carcinomas.

In one aspect, an antibody is provided that specifically binds to denatured CD70 relative to binding to native CD70. In some embodiments, the antibody specifically binds to denatured CD70 on a fixed, ovarian SK-OV-3 or pancreatic PANC-1 cancer cell line relative to binding to native CD70. The antibody can be a monoclonal antibody, such as a chimeric, humanized or human antibody. Preferably, the antibody binds to denatured CD70 on formalin-fixed paraffin embedded cells or tissues with a specific binding that is the same or better than antibody SG-21.1C1 as produced by the hybridoma deposited with the ATCC and assigned Accession No. PTA-8733 or antibody SG-21.5D12 as produced by the hybridoma deposited with the ATCC and assigned Accession No. PTA-8734. In particular, the non-specific cross-reactivity of the antibody is less than that of antibody SG-21.1C1 or antibody SG-21.5D12. In some embodiments, the antibody can compete for specific binding to denatured CD70 with antibody SG-21.1C1 or with antibody SG-21.5D12.

In another aspect, a diagnostic kit is provided that comprises an antibody that specifically binds to denatured CD70 relative to native CD70. In a related aspect, a method of detecting expression of CD70 in a tissue sample of a patient is provided. The tissue sample can be from the pancreas, ovary, lung, larynx, pharynx, breast, kidney, brain, colon, blood or skin from the patient. The issue is fixed and the CD70 protein is denatured. The fixed tissue sample is contacted with an antibody that binds specifically to denatured CD70 relative to native CD70, and the binding of the antibody to the fixed tissue sample is detected to determine whether CD70 is expressed in the sample. Expression of CD70 on the fixed tissue sample indicates a likelihood the patient has a CD70 expressing cancer. In some embodiments, the sample is fixed with formalin and embedded in paraffin.

In another aspect, a method is provided for diagnosing, prognosing, determining a treatment protocol or monitoring treatment of a patient having cancer of the pancreas, ovary, lung, larynx, pharynx, breast, or skin. The method includes determining CD70 expression in cells in a sample from the patient's pancreas, ovaries, lung, larynx, pharynx, breast, or skin of the patient, wherein the presence of detectable CD70 expression is used in the diagnosis, prognosis, determining a treatment protocol or monitoring treatment of the patient. The sample can be a formalin fixed paraffin embedded sample. The method can further include administering an effective regimen of a CD70 antibody or CD70 antibody drug conjugate to the patient if the determining step indicates a detectable level of CD70.

In another aspect, a method of treating a CD70 positive cancer is provided. The method includes administering an effective regimen of a binding agent to CD70 to a patient having cancer of the pancreas, ovary, lung, larynx, pharynx, breast, or skin having detectable expression of CD70, wherein the binding agent is an antibody, antibody derivative or antibody drug conjugate. The antibody may have effector function. The patient may have previously undergone treatment by surgery, radiation and/or chemotherapy with an agent not directed to CD70 without inducing remission of the cancer. In some embodiments, the antibody is a chimeric, humanized, or human antibody, such as a chimeric or humanized form of monoclonal antibody 1F6 or 2F2. The antibody drug conjugate can include a cytotoxic agent, such as an anti-tubulin agent, a DNA minor groove binding agent, or a DNA minor groove alkylating agent. The antibody in the antibody drug conjugate can be conjugated to the cytotoxic or cytostatic agent via a linker, such a linker that is cleavable under intracellular conditions.

In another aspect, a combination diagnostic and pharmaceutical kit comprising an antibody that specifically binds to denatured CD70 for use in diagnosis and an antibody that specifically binds to an extracellular domain of native of CD70 for use in therapy.

Aspects of the invention will best be understood by reference to the following detailed description of the exemplary embodiments, taken in conjunction with the accompanying drawings, figures, and tables.

DEFINITIONS

Figure 1:
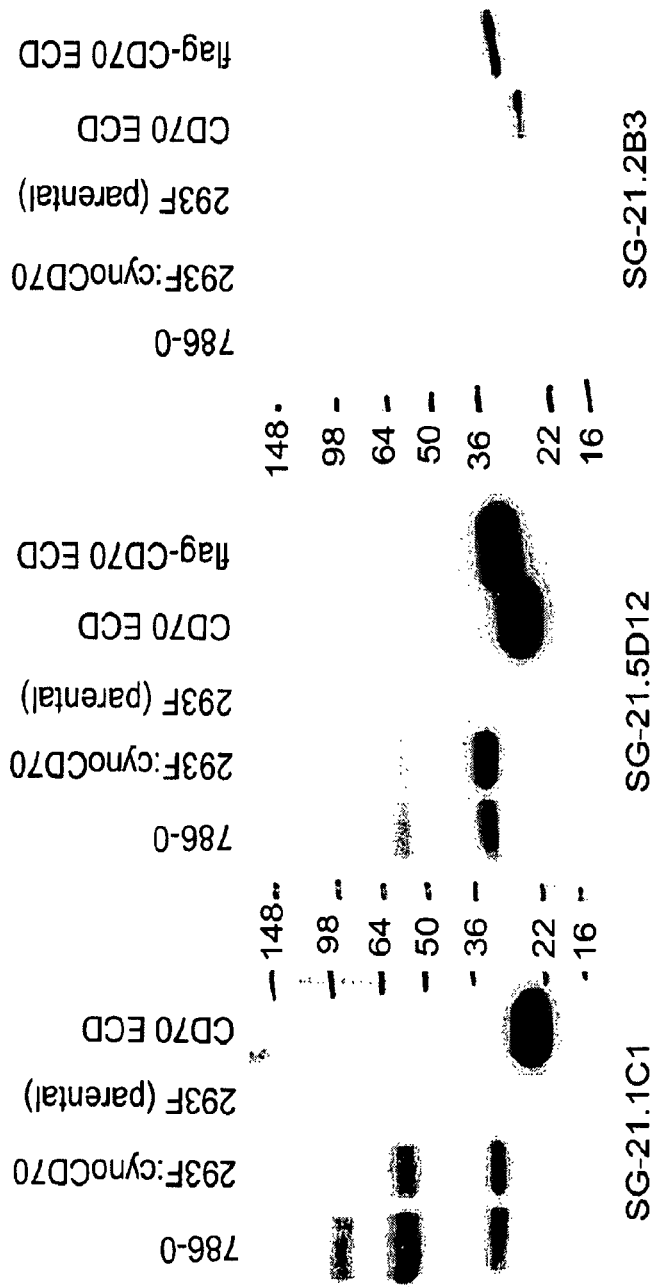
FIG. 1 shows a Western blot of protein extracts using antibodies SG-21.1C1 and SG-21.5D12 to detect denatured CD70 in protein extracts from 786-O, 293F:CD70 transfected cells and 293F untransfected cells.

Unless stated otherwise, the following terms and phrases as used herein are intended to have the following meanings.

The term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD70), or (b) conservatively substituted derivatives of such immunoglobulin polypeptides or fragments that immunospecifically bind to the antigen (e.g., CD70). Antibodies are generally described in, for example, Harlow & Lane, *Antibodies: A Laboratory Manual* (Cold Spring Harbor Laboratory Press, 1988). Unless otherwise apparent from the context reference to an antibody also includes antibody derivatives or drug conjugates as described in more detail below.

An "antibody derivative" means an antibody, as defined above, that is modified by covalent attachment of a heterologous molecule such as, e.g., by attachment of a heterologous polypeptide, or by glycosylation, deglycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

An "antigen" is an entity to which an antibody specifically binds.

The term "inhibit" or "inhibition of" means to a reduce by a measurable amount, or to prevent entirely.

The term "agent" means an element, compound, or molecular entity, including, e.g., a pharmaceutical, therapeutic, or pharmacologic compound. Agents can be natural or synthetic or a combination thereof. A "therapeutic agent" is an agent that exerts a therapeutic (e.g., beneficial) effect on cancer cells, either alone or in combination with another agent (e.g., a prodrug converting enzyme in combination with a prodrug). Typically, therapeutic agents useful in accordance with the methods and compositions described herein are those that exert a cytotoxic or cytostatic effect.

"Cytotoxic effect," in reference to the effect of an agent on a cell, means killing of the cell.

"Cytostatic effect" means an inhibition of cell proliferation.

A "cytotoxic agent" means an agent that has a cytotoxic or cytostatic effect on a cell, thereby depleting or inhibiting the growth of, respectively, cells within a cell population.

The term "deplete," in the context of the effect of a CD70 antibody on CD70-expressing cells, refers to a reduction in the number of, or elimination of, the CD70-expressing cells.

The term "functional," in the context of an anti-CD70 antibody or derivative thereof to be used in accordance with the methods described herein, indicates that the antibody or derivative thereof is (1) capable of binding to CD70 and/or (2) depletes or inhibits the proliferation of CD70-expressing cells alone or when conjugated to a cytotoxic agent.

The term "prophylaxis" refers to administration of an anti-CD70 antibody-drug conjugate (ADC) or ADC derivative to a subject before the onset of a clinical or diagnostic symptom of a CD70-expressing cancer (e.g., administration to an individual with a predisposition or at a high risk of acquiring pancreatic or ovarian cancer) to (a) block the occurrence or onset of the CD70-expressing cancer, or one or more of clinical or diagnostic symptoms thereof, (b) inhibit the severity of onset of the CD70-expressing cancer, or (c) to lessen the likelihood of the onset of the CD70-expressing cancer.

The terms "treatment" or "treat" refer to slowing, stopping, or reversing the progression of a CD70-expressing cancer in a patient, as evidenced by a decrease or elimination of a clinical or diagnostic symptom of the disease, by administration of an anti-CD70 antibody, antibody drug conjugate or ADC derivative to the subject after the onset of the clinical or diagnostic symptom of the CD70-expressing cancer at any clinical stage. Treatment can include, for example, a decrease in the severity of a symptom, the number of symptoms, or frequency of relapse.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which a CD70 antibody is administered.

The term "effective amount," in the context of the administration of a pharmaceutical agent refers to the amount of the agent that is sufficient to inhibit the occurrence or ameliorate one or more clinical or diagnostic symptoms of a CD70-expressing pancreatic or ovarian cancer in a patient. An effective amount of an agent is administered according to the methods described herein in an "effective regimen." The term "effective regimen" refers to a combination of amount of the agent and dosage frequency adequate to accomplish treatment of a CD70-expressing cancer.

The term "patient" includes human and other mammalian subjects that receive diagnostic, prophylactic or therapeutic treatment.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleunine-dolaproine-phenylalanine.

The abbreviations "fk" and "phe-lys" refer to the dipeptide phenylalanine-lysine.

The abbreviations "vc" and "val-cit" refer to the dipeptide valine-citrulline.

Therapeutic agents are typically substantially pure from undesired contaminants. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% purity w/w can be obtained.

DETAILED DESCRIPTION

I. General

The invention provides methods of diagnosis, prognosis, prophylaxis and treatment and monitoring treatment of ovarian and pancreatic cancer using antibodies to CD70. The invention further provides methods of diagnosis, prognosis, prophylaxis and treatment and monitoring treatment of lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal and bladder carcinomas. The methods are premised in part on the results presented in the Examples showing that CD70 is expressed at elevated levels in certain cancers. The elevated expression was detected in formalin fixed paraffin embedded (FFPE) samples from ovarian and pancreatic cancer tissues using antibodies that specifically bind to denatured CD70. Further, elevated expression of CD70 was also detected in formalin fixed paraffin embedded (FFPE) samples from other cancer tissues using antibodies against the denatured extracellular domain of CD70.

Although practice of the invention is not dependent on understanding of mechanism, it is believed that the success in detecting CD70 in FFPE samples of ovarian and pancreatic tissues in particular, and other cancers in general, resides in the use of antibodies that preferentially bind to denatured CD70 in such samples relative to native CD70. Although the frequency of detectable CD70 in pancreatic and ovarian cancer and/or its level are not as high as some other cancerous tissues with which CD70 has been previously associated, they are very specific for cancerous tissue relative to normal tissue. Thus, in patients having ovarian cancer or pancreatic cancer in which CD70 is detectable, CD70 presents a particularly useful target for selectively directing toxicity to cancerous cells. Similarly, in patients having other cancers (such as lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal and bladder carcinomas), the present invention provides a facile way to detect CD70 expression in fixed samples from such patients.

II. Antibodies to CD70

The description that follows first considers properties of antibodies to CD70 applicable to detection of CD70 in ovarian and pancreatic cancers and treatment thereof, and then focuses on preferred properties of antibodies for the respective applications.

A. Antibodies to CD70 in General

Anti-CD70 antibodies include monoclonal, chimeric (e.g., having a human constant region and mouse variable region), humanized, veneered, or human antibodies; single chain antibodies, or the like. The immunoglobulin molecules can be of any type or class (e.g., IgG, IgE, IgM, IgD, IgA and IgY) or subclass (e.g., IgG1, IgG2, IgG3, IgG4, IgA1 and IgA2).

Anti-CD70 antibodies can be an antigen-binding antibody fragment such as, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, including nanobodies or fragments from camels, llamas or the like, or fragments produced by a Fab expression library, or a CD70-binding fragments of any of the above antibodies described supra. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Typically, the antibodies are human, rodent (e.g., mouse and rat), donkey, sheep, rabbit, goat, guinea pig, camelid, horse, or chicken.

The antibodies can be mono-specific, bi-specific, tri-specific, or of greater multi-specificity. Multi-specific antibodies maybe specific for different epitopes of CD70 or may be specific for both CD70 as well as for a heterologous protein. (See, e.g., WO 93/17715; WO 92/08802; WO 91/00360; WO 92/05793; Tutt et al., 1991, J. Immunol. 147:60-69; U.S. Pat. Nos. 4,474,893; 4,714,681; 4,925,648; 5,573,920; and 5,601, 819; Kostelny et al., 1992, J. Immunol. 148:1547-1553.) Multi-specific antibodies, including bi-specific and tri-specific antibodies, useful for practicing the methods described herein are antibodies that immunospecifically bind to both CD70 and a second cell surface receptor or receptor complex, such as an immunoglobulin gene superfamily member, a TNF receptor superfamily member, an integrin, a cytokine receptor, a chemokine receptor, a major histocompatibility protein, a lectin (C-type, S-type, or I-type), or a complement control protein.

Anti-CD70 antibodies can also be described in terms of their binding affinity to CD70, of $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

An anti-CD70 antibody can be a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, *Science*, 1985, 229: 1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

An anti-CD70 antibody can also be a humanized antibody including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riecbmann et al., 1988, *Nature* 332:323.) Antibodies can be humanized using a variety of techniques known in the art such as CDR-grafting (EP 0 239 400; WO 91/09967; U.S. Pat. Nos. 5,225,539; 5,530,101; and 5,585,089), veneering or resurfacing (EP 0 592 106; EP 0 519 596; Padlan, Molecular Immunology, 1991, 28(4/5):489-498; Studnicka et al., 1994, Protein Engineering 7(6):805-814; Roguska et al., 1994, PNAS 91:969-973), and chain shuffling (U.S. Pat. No. 5,565,332) (all of these references are incorporated by reference herein).

An anti-CD70 antibody can also be a human antibody. Human antibodies can be made by a variety of methods known in the art such as phage display methods (see supra) using antibody libraries derived from human immunoglobulin sequences. See also, e.g., U.S. Pat. Nos. 4,444,887 and 4,716,111; WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, *Biotechnology* 12:899-903). Human antibodies can also be produced using transgenic mice that express human immunoglobulin genes. Monoclonal antibodies directed against the antigen can be obtained from the immunized, transgenic mice using hybridoma technology. For an overview of the technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598, 877; and U.S. Pat. Nos. 5,413,923; 5,625,126; 5,633,425; 5,569,825; 5,661,016; 5,545,806; 5,814,318; 5,885,793; 5,916,771; and 5,939,598.

Antibodies can be assayed for specific binding to CD70 by known methods, such as for example, competitive and non-competitive immunoassay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays. (See, e.g., Ausubel et al., eds., *Short Protocols in Molecular Biology* (John Wiley & Sons, Inc., New York, 4th ed. 1999); Harlow & Lane, *Using Antibodies: A Laboratory Manual* (Cold Spring Harbor Laboratory Press, Cold Spring Harbor, N.Y., 1999.)

Further, the binding affinity of an antibody to CD70 and the off-rate of an antibody CD70 interaction can be determined by competitive binding assays. One example of a competitive binding assay is a radioimmunoassay comprising the incubation of labeled CD70 (e.g., $^3$H or $^{125}$I) with the antibody of interest in the presence of increasing amounts of unlabeled CD70, and the detection of the antibody bound to the labeled CD70. The affinity of the antibody for CD70 and the binding off-rates can then be determined from the data by Scatchard plot analysis. Competition with a second antibody can also be determined using radioimmunoassays. In this case, CD70 is incubated with the antibody of interest conjugated to a labeled compound (e.g., $^3$H or $^{125}$I) in the presence of increasing amounts of an unlabeled second antibody. Alternatively, the binding affinity of an antibody to CD70 and the on- and off-rates of an antibody-CD70 interaction can be determined by surface plasmon resonance.

Antibodies can be made from antigen-containing fragments of the CD70 protein by standard procedures according to the type of antibody (see, e.g., Kohler, et al., Nature, 256: 495, (1975); Harlow & Lane, *Antibodies, A Laboratory Manual* (C.S.H.P., NY, 1988); Queen et al., *Proc. Natl. Acad. Sci. USA* 86:10029-10033 (1989) and WO 90/07861; Dower et al., WO 91/17271 and McCafferty et al., WO 92/01047 (each of which is incorporated by reference for all purposes). As an example, monoclonal antibodies can be prepared using a wide variety of techniques including, e.g., the use of hybridoma, recombinant, and phage display technologies, or a combination thereof. Hybridoma techniques are generally discussed in, e.g., Harlow et al., supra, and Hammerling, et al., *In Monoclonal Antibodies and T-Cell Hybridomas*, pp. 563-681 (Elsevier, N.Y., 1981). Examples of phage display methods that can be used to make the anti-CD70 antibodies include, e.g., those disclosed in Briinnan et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, Gene 187:9-18; Burton et al., 1994, *Advances in Immunology* 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Techniques for generating antibody fragments that recognize specific epitopes are also generally known in the art. For example, Fab and F(ab')$_2$ fragments can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain. Techniques to recombinantly produce Fab, Fab' and F(ab')$_2$ fragments can also be employed using, e.g., methods disclosed in WO 92/22324; Mullinax et al., 1992, BioTechniques 12(6):864-869; and Sawai et al., 1995, AJRI 34:26-34; and Better et al., 1988, Science 240: 1041-1043 (the disclosures of which are incorporated by reference herein).

Examples of techniques that can be used to produce single-chain Fvs and antibodies include those described in U.S. Pat.

Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Anti-CD70 antibodies and derivatives thereof that are useful in the present methods can also be produced by recombinant expression techniques. Recombinant expression of an antibody or derivative thereof that binds to CD70 and/or depletes or inhibits the proliferation of CD70-expressing cells requires construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); Ausubel et al., *Short Protocols in Molecular Biology* (John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD70 antibody, an expression vector may encode a heavy or light chain thereof, or a heavy or light chain variable domain, operably linked to a promoter. An expression vector may include, e.g., the nucleotide sequence encoding the constant region of the antibody molecule (see, e.g., WO 86/05807; WO 89/01036; and U.S. Pat. No. 5,122,464), and the variable domain of the antibody may be cloned into such a vector for expression of the entire heavy or light chain. The expression vector is transferred to a host cell by known techniques, and the transfected cells are then cultured to produce the anti-CD70 antibody. Typically, for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD70 antibody or derivative thereof. Typically eukaryotic cells, particularly for whole recombinant anti-CD70 antibody molecules, are used for the expression of the recombinant protein. For example, mammalian cells such as Chinese hamster ovary cells (CHO) (e.g., DG44 or CHO-S) in conjunction with a vector such as the major intermediate early gene promoter element from human cytomegalovirus or the Chinese hamster ovary EF-1α promoter, is an effective expression system for the production of anti-CD70 antibodies and derivatives thereof (see, e.g., Foecking et al., 1986, *Gene* 45:101; Cockett et al., 1990, *Bio/Technology* 8:2; Allison, U.S. Pat. No. 5,888,809).

Other host-expression systems include, plasmid-based expression systems in bacterial cells (see, e.g., Ruther et al., 1983, *EMBO* 1, 2:1791; Inouye & Inouye, 1985, *Nucleic Acids Res.* 13:3101-3109; Van Heeke & Schuster, 1989, *J. Biol. Chem.* 24:5503-5509); insect systems such as the use of *Autographa californica* nuclear polyhedrosis virus (AcNPV) expression vector in *Spodoptera frugiperda* cells; and viral-based expression systems in mammalian cells, such as, adenoviral-based systems (see, e.g., Logan & Shenk, 1984, *Proc. Natl. Acad. Sci. USA* 81:355-359; Bittner et al., 1987, *Methods in Enzymol.* 153:51-544).

B. Antibodies for Detection of CD70

Selection of antibodies to CD70 for use in detection methods depends on whether CD70 is detected by a technique that requires detection of denatured CD70 or native CD70 (as expressed on cells). In methods, such as Western blotting or immunohistochemical detection in which the target CD70 is denatured, it is preferable to use an antibody that binds to CD70 in denatured form (e.g., human or cynomolgus CD70). Typically such antibodies preferentially bind to the denatured form over the native form (i.e., CD70 as it occurs in nature or when isolated without exposure to denaturing conditions, such as solvents, detergents or elevated temperatures (e.g., over 50° C.)). Such antibodies can be raised using a denatured CD70 immunogen (e.g., human or cynomolgus CD70), or an immunogenic fragment thereof from the extracellular portion. Denaturation can be effected by treating the immunogen with SDS (e.g., 0.5%) and optionally heating up to 80° C. Denaturation can also be effected simply by eluting an immunogen from an SDS gel used to purify the immunogen. Alternatively, antibodies preferentially binding to denatured CD70 can be produced using synthetic peptides from the extracellular domain of CD70 as immunogens. Some such peptides are too short to retain the conformation of a corresponding segment of the native peptide. Synthetic peptides can be but do not usually require denaturation to use as an immunogen.

Antibodies generated by these or other methods are screened for preferential binding to denatured CD70 relative to native CD70. Denatured and native CD70 antigen can be assayed by the same assay or by different assays. Particularly, if the latter approach is used, the screening can be performed with a control antibody known to bind native CD70, such as therapeutic antibodies described below (e.g., humanized 1F6 or 2F2; see U.S. Patent Application Publications Nos. 2006-0233794 and 2006-0083736 and International Patent Publication WO 06/113909). If an antibody shows a higher ratio of binding to denatured CD70 relative to native CD70 relative to the ratio of the control antibody, then the antibody preferentially binds to denatured CD70.

Preferred antibodies for detection of CD70 in pancreatic and ovarian cancers are those that specifically bind to CD70 on pancreatic or ovarian cancer specimens that are fixed with formalin and embedded in paraffin (FFPE). These antibodies preferentially recognize epitopes on CD70 that are revealed by the FFPE treatment relative to native CD70 antigens on untreated pancreatic or ovarian cancer cells. Such antibodies are referred to as FFPE-specific anti-CD70 antibodies. Such antibodies lack detectable specific binding to native CD70. Preferably, the specific binding of the antibodies is same or better than antibody SG-21.1C1 or SG-21.5D12. In particular, the antibodies preferably have the same or lower detectable cross-reactivity to other cellular proteins, as determined by Western blot or staining of fixed cells, under specific binding conditions, as compared to antibodies SG-21.1C1 or SG-21.5D12.

Preferred antibodies for detection of CD70 in other cancers (as described infra in the Examples) are those which specifically bind to CD70 in these cancer specimens that are fixed with formalin and embedded in paraffin (FFPE). These antibodies preferentially recognize epitopes on CD70 that are revealed by the FFPE treatment relative to native CD70 antigens on untreated pancreatic or ovarian cancer cells. Such antibodies lack detectable specific binding to native CD70. Preferably, the specific binding of the antibodies is same or better than antibody SG-21.1C1 or SG-21.5D12. In particular, the antibodies preferably have the same or lower detectable cross-reactivity to other cellular proteins, as determined by Western blot or staining of fixed cells, under specific binding conditions, as compared to antibodies SG-21.1C1 or SG-21.5D12.

Some exemplary FFPE-specific anti-CD70 antibodies are mAbs SG-21.1C1 (also referred to as SG-21.1C1-B3) and SG-21.5D12.C3 (also referred to as SG-21.5D12.C3). Other preferred antibodies compete with SG-21.1C1.B3 or SG-21.5D12.C3 for specific binding to denatured CD70. Other preferred antibodies comprise a heavy chain comprising the three CDRs from the heavy chain of SG-21.1C1.B3 and a light chain comprising the three CDRs from the light chain of SG-21.1C1.B3. Other preferred antibodies comprise a heavy chain comprising the three CDRs from the heavy chain of SG-21.5D12.C3 and a light chain comprising the three CDRs from the light chain of SG-21.5D12.C3. Other preferred antibodies comprise a mature heavy chain variable region having at least 90% sequence identity to the mature heavy chain variable region of SG-21.1C1.B3 and a mature light chain variable region having at least 90% sequence identity to the mature light chain variable region of SG-21.1C1.B3. Other preferred antibodies comprise a mature heavy chain variable region having at least 90% sequence identity to the mature heavy chain variable region of SG-21.5D12.C3 and a mature light chain variable region having at least 90% sequence identity to the mature light chain variable region of SG-21.5D12.C3.

C. Antibodies to CD70 for Therapeutic Applications

Antibodies used for therapeutic applications specifically bind to an extracellular domain of native CD70 antigens on pancreatic or ovarian cancer cells. Antibodies used for therapeutic applications can also specifically bind to an extracellular domain of native CD70 antigen on lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal and bladder carcinomas. The antibodies can be agonistic, non-agonistic or antagonistic with respective to CD70 binding to its ligand CD27. Although practice of the invention is not dependent on an understanding of mechanism, it is believed that the antibodies can exert a cytotoxic or cytostatic effect either as a result of binding to CD70 and being internalized within a cell, or by binding to CD70 and accumulating on the outside of cells. In either event, the cytotoxic or cytostatic effect can be promoted by conjugating the antibody to a cytotoxic or cytostatic agent. The cytotoxic or cytostatic effect exerted from the outside of the cell by an antibody bound to CD70 can additionally or alternatively be promoted by an antibody constant (effector) function. The antibody constant domains mediate various Ig effector functions, such as participation of the antibody in antibody dependent cellular cytotoxicity (ADCC), complement dependent cytotoxicity (CDC) and/or antibody dependent cellular phagocytosis (ADCP). Optionally, the effector function of a CD70-binding agent can be augmented by several approaches as described in WO2006/113909. The cytotoxic or cytostatic effect exerted by the antibodies also can be promoted by blocking interaction of CD70 with its ligand, CD27.

A preferred anti-CD70 antibody is mAb 1F6 or 2F2, or a chimeric or humanized forms thereof, as described in WO 2004/073656 and Published US Application No. 2006-0233794 and in WO2006/113909. A preferred heavy chain mature variable region has the sequence of SEQ ID NO: 1 and a preferred light chain mature variable region has the sequence of SEQ ID NO:2.

Other useful antibodies comprise mature heavy and light chain variable regions having at least 90% and preferably at least 95% or 99% sequence identity to SEQ ID NO: 1 and 2, respectively. Guidance as to which residues variable region framework residues are needed for binding is provided by WO2006/113909. Other useful anti-CD70 antibodies or derivatives thereof can competitively inhibit binding of mAb 1F6 or 2F2 to CD70, as determined, for example, by immunoassay. Competitive inhibition means that an antibody when present in at least a two fold and preferably five-fold excess inhibits binding of 1F6 or 2F2 to CD70 by at least 50%, more typically at least 60%, yet more typically at least 70%, and most typically at least 75%, or the antibody competitively inhibits binding of 1F6 or 2F2 to CD70 by at least 80%, at least 85%, at least 90%, or at least 95%.

Other preferred antibodies comprise a heavy chain comprising the three CDRs from the heavy chain variable region of 1F6 and a light chain comprising the three CDRs from the light chain variable of 1F6. Other preferred antibodies comprise a mature heavy chain variable regions having at least 90% sequence identity to the mature heavy chain variable region of 2F2 and a mature light chain variable region having at least 90% sequence identity to the mature light chain variable region of 2F2. Other preferred antibodies comprise a mature heavy chain variable regions having at least 90, 95 or 99% sequence identity to the mature heavy chain variable region of 1F6 and a mature light chain variable region having at least 90, 95 or 99% sequence identity to the mature light chain variable region of 1F6. Other preferred antibodies comprise a mature heavy chain variable region having at least 90, 95 or 99% sequence identity to the mature heavy chain variable region of 2F2 (SEQ ID NO:3) and a mature light chain variable region having at least 90, 95 or 99% sequence identity to the mature light chain variable region of 2F2 (SEQ ID NO:4).

Numerous other antibodies to CD70 are described in, for example, U.S. Patent Application Publication No. 2005-0191299; and International Publication No. WO 07/038,637. Other antibodies binding to an extracellular domain of CD70 can be screened for suitability either alone or as derivatives and/or conjugates as described below. Screening can assess internalization into cells expressing CD70 using labeled antibodies. Screening can also assess cytotoxicity. Additional screening can be performed on animal models of pancreatic or ovarian cancer and other cancers. For example, SKOV-3 ovarian carcinoma cell line, AN3CA endometrial carcinoma cell line, TOV21G ovarian carcinoma cell, can be used. Also, PANC1 and MiaPaca2 pancreatic cell lines can be used.

A derivative of an anti-CD70 antibody can also be used in the practice of present methods. Typical modifications include, e.g., glycosylation, deglycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by, for example, specific chemical cleavage, acetylation, formylation or metabolic synthesis in the presence of tunicamycin. Additionally, the derivative may contain one or more non-classical amino acids.

The antibody derivative can be a multimer, such as a dimer, comprising one or more monomers, where each monomer includes (i) an antigen-binding region of an anti-CD70 antibody, or a polypeptide region derived therefrom (e.g., by conservative substitution of one or more amino acids), and (ii) a multimerizing (e.g., dimerizing) polypeptide region, such that the antibody derivative forms multimers (e.g., homodimers) that specifically bind to CD70. Typically, an antigen binding region of an anti-CD70 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing CD70-expressing cancers, the derivative is subjected to conditions that allows formation of a homodimer or heterodimer. A heterodimer may comprise identical dimerization domains but different CD70 antigen-binding regions, identical CD70 antigen-binding regions but different dimerization domains, or different CD70 antigen-binding regions and dimerization domains.

An anti-CD70 antibody derivative can be formed by conjugating an anti-CD70 antibody to a second antibody (an "antibody heteroconjugate") (see, e.g., U.S. Pat. No. 4,676,980). Heteroconjugates useful for practicing the present methods comprise an antibody that binds to CD70 (e.g., an antibody that has the CDRs and/or heavy chains of the monoclonal antibodies 1F6 or 2F2) and an antibody that binds to a surface receptor or receptor complex, such as an immunoglobulin gene superfamily member, a TNF receptor superfamily member, an integrin, a cytokine receptor, a chemokine receptor, a major histocompatibility protein, a lectin (C-type, S-type, or I-type), or a complement control protein.

Antibodies to CD70 and their derivatives can be conjugated to a cytotoxic or cytostatic moiety to form an antibody drug conjugate (ADC). Particularly suitable moieties for conjugation to antibodies or antibody derivatives are chemotherapeutic agents, prodrug converting enzymes, radioactive isotopes or compounds, or toxins. For example, an anti-CD70 antibody or derivative thereof can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin).

The anti-CD70 antibody or derivative thereof can be conjugated to a pro-drug converting enzyme. The pro-drug converting enzyme can be recombinantly fused to the antibody or derivative thereof or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Dekker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

The therapeutic agent can be conjugated in a manner that reduces its activity unless it is cleaved off the antibody (e.g., by hydrolysis, by antibody degradation or by a cleaving agent). Such therapeutic agent is attached to the antibody or derivative thereof with a cleavable linker that is sensitive to cleavage in the intracellular environment of the CD70-expressing cancer cell but is not substantially sensitive to the extracellular environment, such that the conjugate is cleaved from the antibody or derivative thereof when it is internalized by the CD70-expressing cancer cell (e.g., in the endosomal or, for example by virtue of pH sensitivity or protease sensitivity, in the lysosomal environment or in the caveolear environment).

Typically, the ADC comprises a linker region between the therapeutic agent and the anti-CD70 antibody or derivative thereof. As noted supra, typically, the linker is cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, *Pharm. Therapeutics* 83:67-123). Most typical are peptidyl linkers that are cleavable by enzymes that are present in CD70-expressing cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly peptide). Other such linkers are described, e.g., in U.S. Pat. No. 6,214,345. In specific embodiments, the peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

The linker can also be a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

The linker also can be a non-cleavable linker, such as an maleimido-alkylene- or maleimide-aryl linker that is directly attached to the Drug unit. An active drug-linker is released by degradation of the antibody.

Typically, the linker is not substantially sensitive to the extracellular environment meaning that no more than about 20%, typically no more than about 15%, more typically no more than about 10%, and even more typically no more than about 5%, no more than about 3%, or no more than about 1% of the linkers in a sample of the ADC is cleaved when the ADC or ADC derivative present in an extracellular environment (e.g., in plasma). Whether a linker is not substantially sensitive to the extracellular environment can be determined, for example, by incubating independently with plasma both (a) the ADC or ADC derivative (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivate as described herein). Alternatively, the linker can promote cellular internalization when conjugated to both the therapeutic agent and the anti-CD70 antibody or derivative thereof (i.e., in the milieu of the ADC or ADC derivative as described herein).

A variety of linkers that can be used with the present compositions are described in WO 2004-010957 have the form

wherein:
-A- is a stretcher unit;
a is 0 or 1;
each —W— is independently an amino acid unit;
w is independently an integer ranging from 0 to 12;
—Y— is a spacer unit; and
y is 0, 1 or 2.

Representative linkers are depicted within the square brackets of Formulas (Ia) and (Ib; see infra), wherein A-, —W—, —Y—, -D, w and y are as defined above and $R^1$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1-10. Ab is antibody.

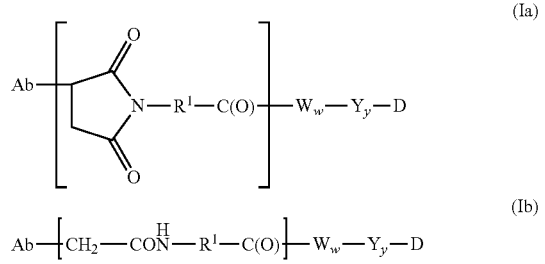

The Amino Acid unit (—W—), if present, links the Stretcher unit (-A-) to the Spacer unit (—Y—) if the Spacer unit is present, and links the Stretcher unit to the cytotoxic or cytostatic agent (Drug unit; D) if the spacer unit is absent.

If present, —$W_w$— is a dipeptide, tripeptide, tetrapeptide, pentapeptide, hexapeptide, heptapeptide, octapeptide, nonapeptide, decapeptide, undecapeptide or dodecapeptide unit. w is an integer ranging from 2 to 12.

The Spacer unit (—Y—), when present, links an Amino Acid unit to the Drug unit. Spacer units are of two general types: self-immolative and non self-immolative. A non self-immolative spacer unit is one in which part or all of the Spacer unit remains bound to the Drug unit after enzymatic cleavage of an amino acid unit from the anti-CD70 antibody-linker-drug conjugate or the drug-linker compound. Examples of a non self-immolative Spacer unit include a (glycine-glycine) spacer unit and a glycine spacer unit. When an anti-CD70 antibody-linker-drug conjugate containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from Ab-$A_a$-$W_w$—. To liberate the drug, an independent hydrolysis reaction should take place within the target cell to cleave the glycine-drug unit bond.

Alternatively, an anti-CD70 antibody drug conjugate containing a self-immolative spacer unit can release the drug (D) without the need for a separate hydrolysis step. In these embodiments, —Y— is a p-aminobenzyl alcohol (PAB) unit that is linked to —$W_w$— via the nitrogen atom of the PAB group, and connected directly to -D via a carbonate, carbamate or ether group. Other examples of self-immolative spacers include aromatic compounds that are electronically equivalent to the PAB group such as 2-aminoimidazol-5-methanol derivatives (see Hay et al., 1999, *Bioorg. Med. Chem. Lett.* 9:2237 for examples) and ortho or para-aminobenzylacetals. Spacers can be used that undergo facile cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury, et al., 1984, *J. Med. Chem.* 27:1447) are also examples of self-immolative spacer strategies that can be applied to the anti-CD70 antibody-linker-drug conjugates. Alternatively, the spacer unit is a branched bis(hydroxymethyl)styrene (BHMS) unit, which can be used to incorporate additional drugs.

Useful classes of cytotoxic agents include, for example, anthracyclines, antitubulin agents, DNA minor groove binders, DNA replication inhibitors, chemotherapy sensitizers, or the like.

Examples of useful classes of cytotoxic agents include auristatins, camptothecins, duocarmycins, etoposides, maytansinoids and vinca alkaloids.

Suitable cytotoxic agents include, for example, auristatins (e.g., auristatin E, AFP, MMAF, MMAE), DNA minor groove binders (e.g., enediynes and lexitropsins), duocarmycins, taxanes (e.g., paclitaxel and docetaxel), vinca alkaloids, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD70 antibodies or derivatives thereof.

In exemplary embodiments, the cytotoxic or cytostatic agent can be auristatin E or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of auristatin E and its derivatives are described in, for example, U.S. Patent Application Publication Nos. 2005-0238649 and 2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The ADC or ADC derivative can comprise an anti-tubulin agent. Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). (Exemplary auristatins are shown below in Formulas III-XIII. Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

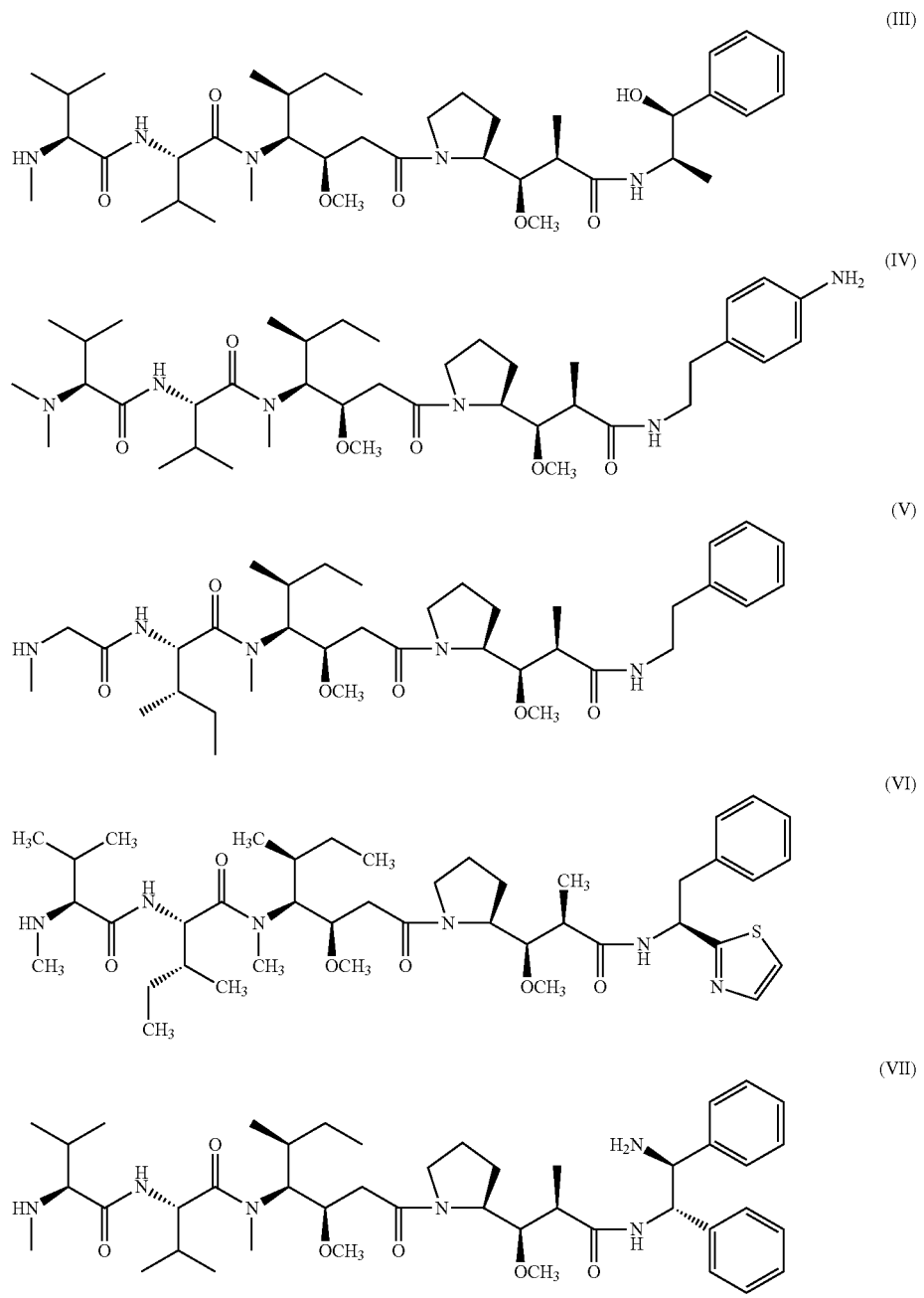

(VIII)
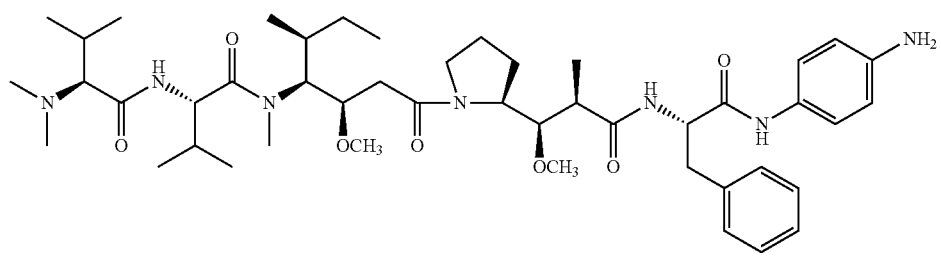
(IX)
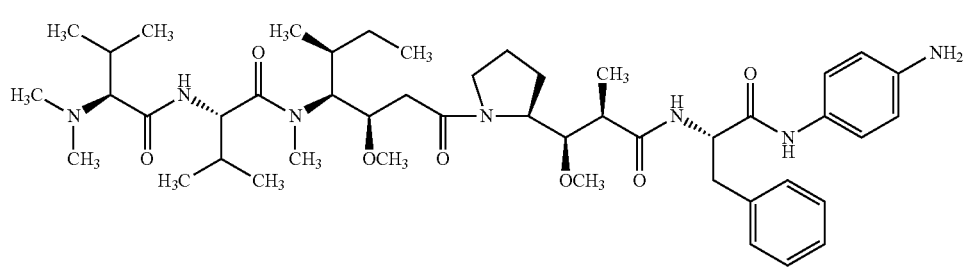
(X)
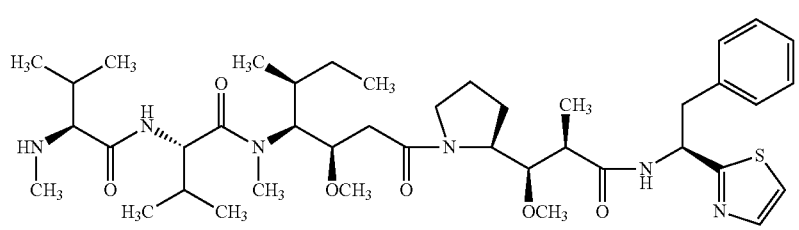
(XI)
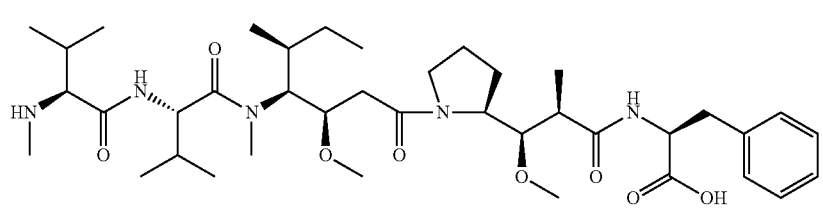
(XII)
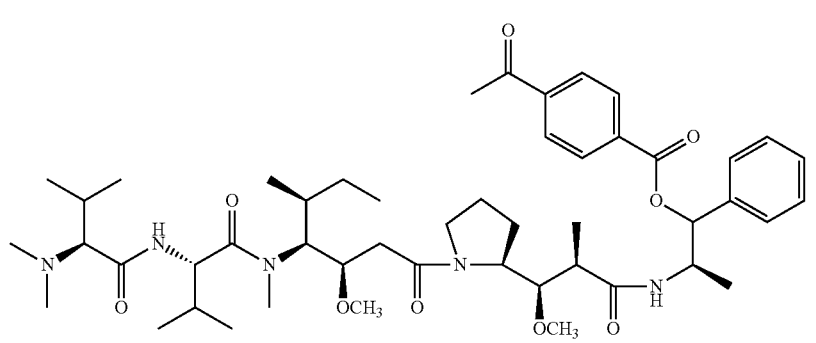
(XIII)
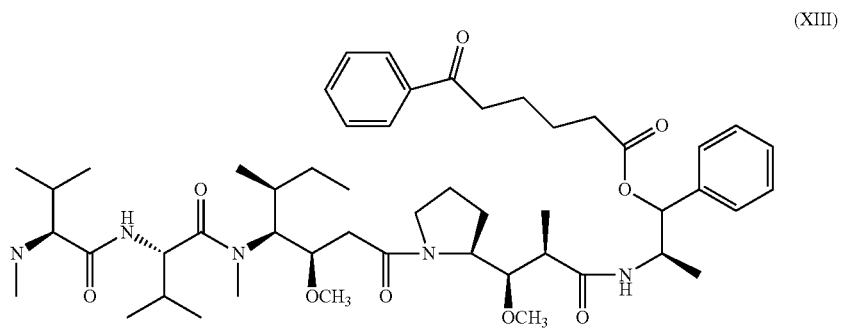 [SMILES: CC[C@H](C)[C@@H]([C@@H](CC(=O)N1CCC[C@H]1[C@H](OC)[C@@H](C)C(=O)N[C@H](C)C(OC(=O)CCCCC(=O)c1ccccc1)c1ccccc1)OC)N(C)C(=O)[C@@H](NC(=O)[C@@H](NC)C(C)C)C(C)C]

The cytotoxic agent can be a maytansinoid, another group of anti-tubulin agents. For example, the maytansinoid is maytansine or a maytansine containing drug linker such as DM-1 or DM-4 (ImmunoGen, Inc.; see also Chari et al., 1992, *Cancer Res.* 52:127-131).

Other binding agents to CD70 can be used as an alternative to antibodies. Such a CD70-targeting moiety can include one or more CDRs from an antibody that binds to CD70 and depletes or inhibits the proliferation of CD70-expressing cells when conjugated to a cytotoxic agent. Typically, the protein is a multimer, most typically a dimer.

Other CD70-targeting moieties can include CD27 and variants or fragments thereof that bind to CD70. CD70-targeting moieties can further include peptides, ligands and other molecules that specifically bind to CD70.

Other CD70-targeting moieties useful in the methods described herein can be identified using any method suitable for screening for protein-protein interactions. Typically, proteins are initially identified by their ability to specifically bind to CD70, then their ability to exert a cytostatic or cytotoxic effect on activated lymphocytes or CD70-expressing cancer cells when conjugated to a cytotoxic or cytostatic agent. Methods that can be employed include "interaction cloning" techniques which entail probing expression libraries with labeled CD70 in a manner similar to the technique of antibody probing of λgt11 libraries. (see, e.g., Blanar and Rutter, 1992, *Science* 256:1014-1018). Another method is the two-hybrid system (Chien et al., 1991, *Proc. Natl. Acad. Sci. USA* 88:9578-9582) and is commercially available from Clontech (Palo Alto, Calif.).

Once a CD70-binding protein is identified, its ability (alone or when multimerized or fused to a dimerization or multimerization domain or conjugated to a cytotoxic or cytostatic moiety) to exert a cytostatic or cytotoxic effect on CD70-expressing cancer cells (when conjugated to a cytotoxic agent) is determined in similar fashion to that for an antibody.

III. Detecting CD70

The samples to be assayed for diagnostic applications can be obtained by surgical procedures, e.g., biopsy. CD70 is typically detected by an immuno assay in which a sample containing cells known or suspected to be from a cancer (e.g., pancreatic or ovarian cancer) is contacted with an antibody. After contact, the presence or absence of a binding event of the antibody to the cells in the specimen is determined. The binding is related to the presence or absence of the antigen expressed on cancerous cells in this specimen. Generally, the sample is contacted with a labeled specific binding partner of the anti-CD70 antibody capable of producing a detectable signal. Alternatively, the anti-CD70 antibody itself can be labeled. Examples of types of labels include enzyme labels, radioisotopic labels, nonradioactive labels, fluorescent labels, toxin labels and chemoluminescent labels. Detection of a signal from the label indicates the presence of the antibody specifically bound to CD70 in the sample.

The sample on which the assay is performed can be fixed or frozen to permit histological sectioning. Preferably, the excised tissue samples are fixed in aldehyde fixatives such as formaldehyde, paraformaldehyde, glutaraldehyde; or heavy metal fixatives such as mercuric chloride. More preferably, the excised tissue samples are fixed in formalin and embedded in paraffin wax prior to incubation with the antibody. An advantage afforded by formalin-fixed paraffin-embedded (FFPE) specimens is the preservation of cellular and architectural morphologic detail in tissue sections (see, e.g., Fox et al., 1985, *J. Histochem. Cytochem.* 33:845-853). Optionally, FFPE specimens can be treated with citrate, EDTA, enzymatic digestion or heat to increase accessibility of epitopes (see, e.g., Shi et al., 1991, *J Histochem Cytochem.* 39:741-748).

Alternatively, a protein fraction can be isolated from cells from known or suspected pancreatic or ovarian cancer and analyzed by ELISA, Western blotting, immunoprecipitation or the like. In another variation, cells can be analyzed for expression of CD70 by FACS analysis, preferably in combination with another pancreatic or ovarian cell marker.

In a further variation, mRNA can be extracted from cells from known or suspected to be pancreatic or ovarian cancers. The mRNA or a nucleic acid derived therefrom, such as a cDNA can then be analyzed by hybridization to a nucleic probe binding to DNA encoding CD70.

In another variation, a pancreatic or ovarian cancer can be detected in vivo by administering a labeled anti-CD70 antibody to a patient and detecting the antibody by in vivo imaging.

Detection of CD70 in tissue samples can be qualitative or quantitative or both. Qualitative detection means detecting the presence or absence of CD70 expression. Quantitative expression means determining a level of expression of expression of CD70. The presence and/or level of CD70 in a pancreatic or ovarian tissue sample at issue can (but need not) be determined with respect to one or more standards. The standards can be historically or contemporaneously determined. The standard can be, for example, a pancreatic or ovarian sample known not to be cancerous from a different subject, a tissue from either the patient or other subject known not to express CD70, or a pancreatic or ovarian cell line. The standard can also be the patient sample under analysis contacted with an irrelevant antibody (e.g., an antibody raised to a bacterial antigen). Because CD70 is not expressed to any significant extent in non-cancerous pancreatic or ovarian tissue, such non-cancerous tissue can be used as a zero (background) expression standard.

The presence of detectable signal from binding of an anti-CD70 antibody to CD70 relative to a standard (if used) indicates the presence of CD70 in the tissue sample, and the level of detectable binding provides an indication of the level of expression of CD70. In assays performed on tissue sections, the level of expression can be expressed as a percentage of the surface area of the sample showing detectable expression of CD70. Alternatively, or additionally, the level (intensity) of expression can be used as a measure of the total expression in the sample or of the cells expressing CD70 in the sample.

IV. Diagnosis, Prognosis, Designing and Monitoring Treatment

Detection of expression of CD70 in a sample of pancreatic or ovarian tissue is an indication that the sample is cancerous. Similarly, detection of expression of CD70 in a other patient sample is an indication that the patient has lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal or bladder carcinoma. Antibodies used for therapeutic applications specifically bind to an extracellular domain of native CD70 antigens.

The indication of cancer provided by presence and/or level of CD70 can be combined with means of diagnosis, such as internal or external examination of a patient by a physician, X-ray, CT Scan (Computed Tomography), PET Scan (Positron Emission Tomography), PET/CT Scan, ultrasound, MRI (Magnetic Resonance Imaging), endoscopy, ERCP (Endoscopic Retrograde Cholangiopancreatography), histological examination and tissue culturing in arriving at an overall diagnosis.

Perhaps of greatest relevance to the physician, the presence and level of CD70 provides useful information for designing a treatment protocol for the patient, and in particular administering an antibody against CD70, a derivative, an ADC or other binding agent to a patient. Because of the essential absence of detectable CD70 expression in normal pancreatic or ovarian tissue, the presence of this receptor in a cancer provides a target for therapeutic treatment. The higher the level of CD70 expression and/or the higher percentage of a tumor expressing CD70, the more effective treatment is likely to be. Continued analysis of CD70 after treatment provides a means of monitoring whether the treatment is effective, a reduction in the level of CD70-positive signal (i.e., as a proxy for the presence of CD70-positive cancer cells) that the treatment is effective.

V. Patients Amenable to Treatment

Patients amenable to treatment by the methods usually have detectable levels of CD70 in their pancreatic, ovarian or other tissue accompanied by other signs or symptoms of cancer as described above. A variety of subtypes and stages of both pancreatic and ovarian cancer exist as described in more detail below. Sometimes, patients treated by the present methods have undergone other types of treatment previously (e.g., surgery, chemotherapy and/or radiation) without inducing remission or even slowing down the growth of the cancer. In some such patients, the cancer is refractory to treatment by one of more such therapies.

Some patients at risk of pancreatic cancer can also be treated prophylactically before signs and symptoms of the disease appear. Such individuals include those having relatives who have experienced these diseases, and those whose risk is determined by analysis of genetic or biochemical markers.

A. Pancreatic Cancer Patients

Pancreatic cancer is a malignant tumor within the pancreatic gland. Almost 90% of pancreatic cancer patients are older than 55. The average age at the time this cancer is found is 72. Risk factors for pancreatic cancer include: age, male gender, African ethnicity, smoking, diets high in meat, obesity, diabetes, chronic pancreatitis (has been linked, but is not known to be causal), occupational exposure to certain pesticides, dyes, and chemicals related to gasoline, family history, *Helicobacter pylori* infection, gingivitis or periodontal disease. (Pancreatic Cancer. Von Hoff et al., ed., Maine; 2005.) Only 10 to 15% of pancreatic cancer is considered hereditary. Some genetic markers that are connected to pancreatic cancer can include mutations in the PNCA1, PALLD or BRCA2 gene (see, e.g., Banke et al., 2000, *Med. Clin. North Am.* 84: 677-690; Meckler et al., 2001, *Am. J. Surg. Path.* 25: 1047-1053; Pogue-Geile et al., 2006, *PLoS Med.* 3: e516; Murphy et al., 2002, *Cancer Res.* 62: 3789-3793).

However, not all patients in the currently recognized risk categories will develop pancreatic cancers. Many pancreatic cancers arise "sporadically" (i.e., in patients without family histories).

Individuals suffering from pancreatic cancer can be recognized according to the histology of the tumor, obtained in a pathology report. Histology dictates many aspects of clinical treatment, management, and prognosis. There are two main types of pancreatic cancer based on whether the tumor starts from the exocrine or endocrine gland of the pancreas. Tumors formed from the exocrine gland of the pancreas are much more common. About 95 percent of pancreatic tumors are adenocarcinomas. The remaining 5 percent include other tumors of the exocrine pancreas (e.g. serous cystadenomas), acinar cell cancers, and pancreatic neuroendocrine tumors (such as insulinomas).

Endocrine tumors are also called islet cell tumors and are divided into several sub-types. Most are benign, but there are a few that are cancerous. A special type of cancer (ampullary cancer) can occur where the bile duct from the liver and the pancreatic duct empty into the small intestine. Because this type of cancer often causes signs such as yellowing of the skin and eyes, it is usually found at an earlier stage than most pancreatic cancers. The chances of successful treatment are better for patients suffering from ampullary cancer.

Pancreatic cancer staging can be performed according to the American Joint Committee on Cancer (AJCC) criteria. The cancer stages are labeled using Roman numerals I through IV, with stage IV indicating that the cancer has spread and is more serious. Specifically, stage I pancreatic cancer includes tumors which have not spread into certain proscribed sensitive areas and which have no involved regional nodes or distal metastasis. Stage II includes tumors which have spread into the duodenum, bile duct, or "peripancreatic" tissues and which have no involved regional nodes or distal metastasis. Stage III cancer includes tumors which may have or may not have spread into these areas and which have involved regional nodes, but which show no evidence of distal metastasis. Stage IVA includes tumors which have spread into the stomach, spleen, large bowel or the adjacent large vessels and which have involved regional nodes, but show no evidence of distal metastasis. Stage IVB includes pancreatic tumors of any kind with node status of any kind and with evidence of distal metastasis. Though referred to, this pancreatic cancer staging system is rarely used in its pure form because the stages do not fully match patient prognosis or treatment options. An alternative is the three stage classification (potentially resectable, locally advanced and metastatic), which is based on radiological findings. Other prognosis factors are also considered. The grade of the cancer which indicates how abnormal the cells look under the microscope is sometimes listed on a scale from G1 to G4, with G1 cancers looking the most like normal cells and having the best outlook. For patients who have surgery, the extent of the resection, i.e., whether or not all of the tumor is removed, is also important with regard to outlook. This is sometimes listed on a scale from R0 to R2 with R0 indicating that all of tumor that can be seen has been removed and R2 indicating that some tumor that can be seen can not be removed.

Early pancreatic cancer symptoms are non-specific and varied. Common symptoms include pain in the upper abdomen that typically radiates to the back and is relieved by leaning forward (seen in carcinoma of the body or tail of the pancreas), loss of appetite, significant weight loss and painless jaundice related to bile duct obstruction (carcinoma of the head of the pancreas). However, all of these symptoms can have multiple other causes and are not limited to pancreatic cancer.

B. Ovarian Cancer Patients

Ovarian cancer is cancer that begins in the ovaries. Ovarian cancer usually happens in women over age 50, but it can also affect younger women. Its cause is unknown. Certain populations such as Ashkenazi Jewish women are at a higher risk, often at an earlier age than the general population. Patients with a personal history of breast cancer or a family history of ovarian, breast, or other related cancers, especially if at a young age, may have an elevated risk. A strong family history of uterine cancer, colon cancer, or other gastrointestinal cancers may indicate the presence of a syndrome known as hereditary nonpolyposis colorectal cancer (HNPCC, also known as Lynch II syndrome), which confers a higher risk for developing ovarian cancer. Cytogenetic studies and loss of heterozygosity investigations suggest that some genes or chromosomal regions are involved in ovarian cancer initiation and progression (see, e.g., Pejovic et al., 1992, *Genes Chromosomes Cancer*, 4:58-68; Testa et al., 1994, *Cancer Res.*, 54:2778-2784: Yang-Feng et al., 1993, *Int. J. Cancer*, 54:546-551). Genetic markers of risk toward ovarian cancer include, but are not limited to mutations in the BRCA1 or the BRCA2 gene (Futreal et al., 1994, *Science*, 266:120-122). Patients with strong genetic risk for ovarian cancer may consider the use of preventative oophorectomy after completion of child-bearing. Not all women in currently recognized risk categories will develop ovarian cancers. The majority of ovarian cancers arise sporadically.

Individuals suffering from ovarian cancer can be recognized according to the histology of the tumor, obtained in a pathology report. Histology dictates many aspects of clinical treatment, management, and prognosis. There are three main types of ovarian cancer based on the kind of cells the tumor started from and whether the tumor is benign or cancerous. Germ cell tumors start from the cells that produce the eggs. Stromal tumors start from connective tissue cells that hold the ovary together and produce the female hormones estrogen and progesterone. Epithelial tumors start from the cells that cover the outer surface of the ovary. Most ovarian cancers are epithelial tumors, with a minority of tumors arising from the germ or stromal cells.

Ovarian cancer often is primary, but can also be secondary, the result of metastasis from a primary cancer elsewhere in the body. For example, from breast cancer, or from gastrointestinal cancer (in which case the ovarian cancer is a Krukenberg cancer). Surface epithelial-stromal tumor can originate in the lining of the abdominal cavity, in which case the ovarian cancer is secondary to primary peritoneal cancer, but treatment is basically the same as for primary ovarian cancer of this type.

In ovarian cancers, the cancer stages are as follows: stage I is limited to one or both ovaries; stage II involves pelvic extension or implants; stage III involves microscopic peritoneal metastases beyond the pelvis; or limited to the pelvis with extension to the small bowel or omentum; and stage IV involves distant metastases such as in the liver, or outside the peritoneal cavity.

Early ovarian cancer is frequently asymptomatic, or produces only mild symptoms which might be ignored by the patient because the symptoms are either vague or non-specific. Symptoms can include bloating, pelvic or abdominal pain, trouble eating or feeling full quickly, urinary symptoms, such as urgent or frequent feelings of needing to go. (See, e.g., Smith et al., 2005, *Cancer* 104(7):1398-1407; The consensus statement released by the American Cancer Society, the Gynecologic Cancer Foundation, and the Society of Gynecologic Oncologists on Jun. 12, 2007.) More than 60% of patients presenting with this cancer already have stage III or stage IV cancer, when it has already spread beyond the ovaries.

C. Other Cancer Patients

Other patients amenable to treatment by the methods usually have detectable levels of CD70 in samples of lung, head and neck (larynx or pharynx), melanoma, glioblastoma, multiple myeloma, Hodgkin lymphoma, non-Hodgkin lymphoma, such as follicular lymphoma, renal cell carcinoma, including clear cell and papillary, colorectal or bladder carcinoma. Such patients may be accompanied by other signs or symptoms of cancer. Sometimes, patients treated by the present methods have undergone other types of treatment previously (e.g., surgery, chemotherapy and/or radiation) without inducing remission or even slowing down the growth of the cancer. In some such patients, the cancer is refractory to treatment by one of more such therapies.

Some patients at risk of cancer can also be treated prophylactically before signs and symptoms of the disease appear. Such individuals include those having relatives who have experienced these diseases, and those whose risk is determined by analysis of genetic or biochemical markers.

VI. Methods of Treatment

The present invention provides methods of treating or prophylaxis of pancreatic or ovarian cancer by the antibodies, derivatives and ADC, and other anti-CD70 binding agents (collectively agents) disclosed herein. The compositions can be administered to a patient.

Various delivery systems can be used to administer the agents including intradermal, intramuscular, intraperitoneal, intravenous, subcutaneous, intranasal, epidural, and oral routes. The agents can be administered, for example by infusion or bolus injection, by absorption through epithelial or mucocutaneous linings (e.g., oral mucosa, rectal and intestinal mucosa, and the like) and can be administered together with other biologically active agents such as chemotherapeutic agents. Administration can be systemic or local.

The agents can be administered by injection, by means of a catheter, by means of a suppository, or by means of an implant, the implant being of a porous, non-porous, or gelatinous material, including a membrane, such as a sialastic membrane, or a fiber.

Alternatively, the agents can be delivered in a controlled release system. For example, a pump can be used (see Langer, 1990, *Science* 249:1527-1533; Sefton, 1989, *CRC Crit. Ref Biomed. Eng.* 14:201; Buchwald et al., 1980, Surgery 88:507; Saudek et al., 1989, *N. Engl. J. Med.* 321:574). Alternatively, polymeric materials can be used (see *Medical Applications of Controlled Release* (Langer & Wise eds., CRC Press, Boca Raton, Fla., 1974); *Controlled Drug Bioavailability, Drug Product Design and Performance* (Smolen & Ball eds., Wiley, New York, 1984); Ranger & Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

The agents can be administered as pharmaceutical compositions comprising a therapeutically or prophylactically effective amount of the agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, pH buffering agents (e.g., amino acids) and/or solubilizing or stabilizing agents (e.g., nonionic surfactants such as tween or sugars such as sucrose, trehalose or the like). These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or a concentrate in a hermetically sealed container such as an ampoule or sachette indicating the quantity of active agent. When the pharmaceutical is to be administered by infusion, it can be dispensed with an infusion bottle containing sterile pharmaceutical grade water or saline. When the pharmaceutical is administered by injection, an ampoule of sterile water for injection or saline can be provided so that the ingredients can be mixed prior to administration.

The amount of the agent that is effective in the treatment or prophylaxis of pancreatic or ovarian cancer can be determined by standard clinical techniques. In addition, in vitro assays may optionally be employed to help identify optimal dosage ranges. The precise dose to be employed in the formulation also depends on the route of administration, and the stage of pancreatic or ovarian cancer, and should be decided according to the judgment of the practitioner and each patient's circumstances. Effective doses may be extrapolated from dose-response curves derived from in vitro or animal model test systems. A dose can be formulated in animal models to achieve a circulating plasma concentration range that includes the $IC_{50}$ (i.e., the concentration of the test compound that achieves a half-maximal inhibition of symptoms) as determined in cell culture.

For example, toxicity and therapeutic efficacy of the agents can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit large therapeutic indices are preferred. When an agent exhibits toxic side effects, a delivery system that targets the agent to the site of affected tissue can be used to minimize potential damage to non-CD70-expressing cells and, thereby, reduce side effects.

Generally, the dosage of an antibody, derivative or ADC administered to a patient with a CD70-expressing cancer is typically 0.1 mg/kg to 100 mg/kg of the subject's body weight. More typically, the dosage administered to a subject is 0.1 mg/kg to 10 mg/kg of the subject's body weight, even more typically 0.1 mg/kg to 5 mg/kg, or 0.1 mg/kg to 3 mg/kg of the subject's body weight. Generally, human antibodies have a longer half-life within the human body than antibodies from other species due to the immune response to the foreign proteins. Thus, lower dosages of ADCs comprising humanized, chimeric or human antibodies and less frequent administration is often possible.

Antibodies to CD70, derivatives and ADCs can also be administered in combination with one or more other therapeutic agents for the treatment or prophylaxis of pancreatic or ovarian cancer. For example, combination therapy can include a second cytostatic or cytotoxic agent (for example, an unconjugated cytostatic or cytotoxic agent such as those conventionally used for the treatment of cancers). Combination therapy can also include, e.g., administration of an agent that targets a receptor or receptor complex other than CD70 on the surface of CD70-expressing cancer cells. Typically, such an antibody or ligand binds to a cell surface receptor on CD70-expressing cancer cells and enhances the cytotoxic or cytostatic effect of the anti-CD70 antibody by delivering a cytostatic or cytotoxic signal to the CD70-expressing cancer cells.

Other drugs that can administered with the agents include growth factor inhibitors, or anti-angiogenesis factors. For example, a drug called erlotinib, an epidermal growth factor receptor tyrosine kinase inhibitor, can be used to treat advanced pancreatic cancer. (Bareschino et al., 2007, *Ann Oncol. Suppl* 6: 35-41.) Such combinatorial administration can have an additive or synergistic effect on disease parameters (e.g., severity of a symptom, the number of symptoms, or frequency of relapse).

The present methods can be combined with other means of treatment such as surgery, radiation, targeted therapy, immunotherapy, use of growth factor inhibitors, or anti-angiogenesis factors.

Surgery is a preferred treatment and is frequently necessary to obtain a tissue specimen for differential diagnosis via its histology. Improved survival is attributed to more accurate staging of the disease and a higher rate of aggressive surgical excision of tumor in the abdomen. The type of surgery depends upon how widespread the cancer is when diagnosed (the cancer stage), as well as the presumed type and grade of cancer.

For patients suffering from pancreatic adenocarcinoma, the surgeon can perform the Whipple procedure (also called, pancreaticoduodenectomy). In this procedure, the head of the pancreas and sometimes the body of the pancreas are removed along with parts of the stomach and small intestine, the gallbladder, part of the common bile duct, and some nearby lymph nodes. (See, e.g., Michalski et al., 2007, *Nat. Clin. Pract. Oncol.* 4(9):526-35.) For patients suffering from endocrine tumors of the pancreas (islet cell tumors), surgery is a viable option. (See, e.g., Akerstrom and Hellman, 2007, *Best Pract. Res. Clin. Endocrinol. Metab.* 21(1):87-109.)

In ovarian cancer patients, the surgeon can remove one (unilateral oophorectomy) or both ovaries (bilateral oophorectomy), the fallopian tubes (salpingectomy) and the uterus (hysterectomy). For some very early tumors such as those in stage I, only the involved ovary and fallopian tube will be removed ("unilateral salpingo-oophorectomy," USO), especially in young females who wish to preserve their fertility. In advanced malignancy, where complete resection is not feasible, as much tumor as possible is removed (debulking surgery). In cases where this type of surgery is successful, the prognosis is improved compared to patients where large tumor masses (more than 1 cm in diameter) are left behind. Minimally invasive surgical techniques can facilitate the safe removal of very large (greater than 10 cm) tumors with fewer complications of surgery. (See, e.g., Ehrlich et al., 2007, *J. Pediatr. Surg.* 42 (5): 890-3.)

Chemotherapy refers to the use of anti-cancer or cytotoxic drugs to kill cancer cells. Chemotherapy can be given to the patient before or after surgery. Depending on the histology of the tumor, some kinds of tumor (particularly teratoma) are not sensitive to chemotherapy. Intravenous chemotherapy with drugs such as, e.g., gemcitabine, 5-fluorouracil, cisplatin or mitomycin C can be used to treat pancreatic cancer. Intravenous chemotherapy such as gemcitabine, topotecan, doxorubicin, liposomal doxorubicin, carboplatin, paclitaxel can be used to treat ovarian cancer. Chemotherapy that is partly intravenous and partly intraperitoneal can also improve median survival time. (*The Chemotherapy Source Book* (3rd edition). Ed. Perry. Lippincott, Williams and Wilkins, 2001; *Oxford Textbook of Palliative Medicine.* (2nd Ed.) Derek Doyle et al. Oxford University Press. 1999.).

Radiation therapy is treatment with high energy rays, such as x-rays, to kill or shrink cancer cells while doing as little harm as possible to normal cells. Radiation can be given to the patient before or after surgery. Radiation therapy can also be used to treat pancreatic cancer which has not spread but cannot be removed by surgery. Radiation therapy is not often used to treat cancer of the ovary, but may occasionally be used, if appropriate. Combination radiation and chemotherapy can be used for patients whose tumors are too widespread to be removed by surgery.

An anti-CD70 antibody, derivative or ADC can be administered concurrently to a patient undergoing surgery, chemotherapy or radiation therapy treatments. Alternatively, a patient can undergo surgery, chemotherapy or radiation therapy prior or subsequent to administration of an anti-CD70 antibody, derivative or ADC by at least an hour and up to several months, for example at least an hour, five hours, 12 hours, a day, a week, a month, or three months, prior or subsequent to administration of the ADC or ADC derivative.

VII. Kits

The invention provides diagnostic kits for use with the above detection methods. The kits typically contain an antibody or fragment thereof that specifically binds to denatured CD70 useful for detection as described above. One or more additional containers may enclose elements, such as reagents or buffers, to be used in the assay. Such kits can also, or alternatively, contain a detection reagent that contains a reporter group suitable for direct or indirect detection of antibody binding.

The invention further provides pharmaceutical kits for treating pancreatic and ovarian cancers. Typically, such kits contain reagents formulated as a therapeutic composition as described herein, and can be in any of a variety of forms suitable for distribution in a kit. Such forms can include a liquid, powder, tablet, suspension and the like formulation for providing the agents, such as anti-CD70 antibodies, derivatives or ADCs. The kits can also include a pharmaceutically acceptable diluent (e.g., sterile water) for injection, reconstitution or dilution of the lyophilized antibody, derivative or ADC.

The invention further provides combined kits for diagnosis and therapy. Such kits typically include at least one antibody that binds preferentially to denatured CD70 over native CD70 for use in detection in fixed tissue sections and a different antibody that binds to native CD70 at least as well if not better than denatured CD70 for use in treatment.

Kits also typically contain a label or instructions for use in the methods of detection and/or treatment described herein. The label or instruction refers to any written or recorded material that is attached to, or otherwise accompanies a kit at any time during its manufacture, transport, sale or use. It can be a notice in the form prescribed by a governmental agency regulating the manufacture, use or sale of pharmaceuticals or biological products, which notice reflects approval by the agency of manufacture, use or sale for human administration. The label or instruction can also encompass advertising leaflets and brochures, packaging materials, instructions, audio or video cassettes, computer discs, as well as writing imprinted directly on the pharmaceutical kits.

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ). Cell culture reagents were obtained from Invitrogen Corp., Carlsbad, Calif., or other suppliers.

EXAMPLES

Example 1

Preparation of Monoclonal Antibodies SG-21.1C1.B3 and SG-21.5D12.C3

Monoclonal antibodies SG-21.1C1.B3 and SG-21.5D12.C3 were produced using B-cells from spleen or lymph nodes removed from a mouse that was challenged several times with the immunogen, denatured extracellular domain of CD70 (CD70-ECD). These B-cells were then fused with myeloma tumor cells to produced hybridomas. Large numbers of monoclonal antibodies were thus produced from these hybridomas. The hybridomas were diluted to ensure clonality and grown.

Antibodies from the different clones were tested for their ability to bind to the denatured CD70 antigen with a test such as an ELISA using Flag-CD70 or a differential FMAT screen (Applied Biosystems, Foster City, Calif.) using fixed 293F expressing cynomolgus monkey ("cyno") CD70 and denatured L540cy cells, which express CD70. Untransfected 293F and L540cy cells were used as a negative control. (Some L540cy cells were positive for CD70).

The results showed that over 100 hybridomas tested positive for their ability to bind to denatured CD70. Antibodies from two positive hybridomas, SG-21.1C1.B3 ("1C1") and SG-21.5D12.C3 ("5D12"), were selected for immunohistochemistry.

Example 2

Preparation of Formalin-Fixed Paraffin Embedded (FFPE) Samples

Formalin-fixed paraffin embedded tissues were prepared according to standard methods, as described in fixed in *Theory and Practice of Histotechnology*, Second Edition. 1980, Sheehan, D. C. and Hrapchak, B. B., editors (Battelle Press (Columbus, Ohio). Chapter 3, pp. 59-78).

The preparation of cells by FFPE was similar to that of the tissue preparation. Briefly, cells were plated in suitable culture media at about 15,000 cells/well 1 day prior to fixation. The cells were fixed as follows: The cells washed 2× with PBS and then fixed with 10% formalin at room temperature for 45 minutes. Afterwards, the cells were washed 2× with PBS and then permeablized with PBS+0.5% Triton X-100 at room temperature for 15 minutes. The cells were then washed 1× with PBS and stored in PBS+0.02% sodium azide at 4° C. Prior to FMAT screening, the PBS+azide was removed and the plate was blocked with PBS+5% goat serum at room temperature for 30 minutes.

Example 3

Preparation of Tissue Microarrays for Immunohistochemistry

Tissue microarrays of FFPE tissue sections were obtained from commercial sources, including US Biomax, TriStar or Cybrdi. Tissue microarray are also prepared according to the Yale Tissue Microassay Construction Protocols, Version 1.0, and later updates.

Example 4

Development of Monoclonal Antibodies SG-21.1C1.B3 and SG-21.5D12.C3 as Immunohistochemistry Reagents for FFPE Samples A. Immunohistochemical Testing of CD70 Clones An expression construct encoding cynomolgus monkey CD70 was made by cloning a full-length cynomolgus CD70 gene into an expression vector. This construct was transfected into 293F cells. These 293F:CD70 transfected cells served as the positive control for staining with 1C1 and 5D12 antibodies. The parental 293F cell line served as the negative control. For tissue staining, 786-O cells, that express CD70, served as the positive control.

The cells and tissues were fixed and embedded in paraffin wax according to the procedure described in Example 2. IHC staining and antigen retrieval was performed using a Vision BioSystems Bond-max™ system (now Leica Microsystems). Antigen retrieval was performed for 40 minutes using the EDTA retrieval method. Alternatively, antigen retrieval was performed using the Trilogy antigen retrieval system (Cell Marque, Hot Springs, Ark.) at a temperature of 99-100° C. for 1 hour.

Both the 1C1 primary antibody or the 5D12 primary antibody stained strongly all fixed 293F:CD70 transfected cells, whereas no staining was detected in the parental 293 cells. The results also showed strong staining in the 786-O cells (a renal cell carcinoma) whereas background staining was detected in a Ramos xenograft control.

The 1C1 clone was further subcloned and a subclone, 1C1-B3 (SG-21.1C1.B3) was selected. Likewise, 5D12 was further subcloned and a subclone, 5D12-C3 (SG-21.5D12.C3) was selected. These two subclones were purified and used as primary antibodies to stain 786-O xenograft and Ramos xenograft samples. The results showed that subcloning and purification of 1C1-B3 and 5D12-C3 removed background staining in the Ramos xenograft.

Hybridomas producing the anti-CD70 antibodies have been deposited with the American Type Culture Collection (ATCC) at 10801 University Boulevard, Manassas, Va. 20110-2209. The cell line designated SG-21.1C1.B3, producing the antibody 1C1 having the ATCC accession number PTA-8733 has been deposited on Oct. 24, 2007 at the ATCC; the cell line designated SG-21.5D12.C3 producing the antibody 5D12 having the ATCC accession number PTA-8734 has been deposited on Oct. 24, 2007 at the ATCC. The deposits were made in accordance with the provisions of the Budapest Treaty on the International Recognition of the Deposit of Microorganisms for the Purposes of Patent Procedure.

B. Western Blotting with SG-21 Antibodies 1C1 and 5D12 Compared with 2B3 Antibody To determine whether SG-21 antibodies 1C1 and 5D12 antibodies detect CD70 in cell and tissue lysates, Western blots experiments were conducted. Another CD70 binding antibody, 2B3, was also used for comparison. Membrane preparations were prepared from 786-O cells, 293F:cyn-oCD70 (expressing cyno CD70) cells and 293F cells as a negative control. To prepare membrane extracts, cell were lysed in hypotonic buffer solution and centrifuged at 10,000×g for 10 minutes at 4° C. to remove debris. The supernatants were then centrifuged at 100,000×g for 30 minutes at 4° C. to pellet the membrane fractions. The membrane fractions (pellet) were dissolved in 0.5% NP40 in 50 mM Tris plus 150 mM NaCl and 5 mM EDTA. All sample preparation was done in the presence of protease inhibitors to keep CD70 intact. The quantity of the proteins was measured at 570 nm using a BCA Kit (Pierce). CD70 ECD (extracellular domain of CD70) and Flag tagged CD70-ECD were also prepared by standard methods. The protein samples were denatured at 90° C. for 3 minutes and chilled on ice for 3 minutes. The samples were separated using SDS-PAGE and then transferred to a nitrocellulose membrane for detection. Four identical SDS-PAGE gels and membranes were prepared. The membranes were blocked in PBS with 1% BSA and 2% non-fat milk with 0.05% Tween (polysorbate). Each primary antibody was then added to the solution at 0.5 µg/ml and allowed to incubate for 4 hours at room temperature in PBS with 0.05% Tween. The membranes were washed and a secondary antibody-enzyme conjugate, which recognized the primary antibody was added and incubated for 45 minutes at room temperature. The membranes were washed and incubated with a chemiluminescent substrate to detect CD70.

Referring to FIG. 1, the results showed that SG-21 antibodies 1C1 and 5D12 antibodies detected CD70 in the 786-O and the 293F:CD70 transfectants, but not in the negative control 293F cells. Notably, the detected bands were of identical size in the 786-O and 293F:CD70 transfectants. SG-21 antibody 2B3 did not detect CD70 in 786-O and 293:cyn-oCD70 samples but detected CD70ECD and flag-CD70-ECD. The result indicated that 1C1 and 5D12 antibodies detected CD70 in the samples.

C. CD70 Expression in Tumor and Non-Tumor Cell Lines Using SG21.1C1 Antibody

Tissue microarrays were obtained from commercial sources or custom prepared that contained samples of the following cancers: Breast Carcinoma, Ovarian Carcinoma, Mesothelioma, Osteosarcoma, Prostate Carcinoma, Hepatocellular Carcinoma, Glioblastoma, Anaplastic Astrocytonma, Uterine Cancer, Embryonic Cancer, Epidermoid Carcinoma, Multiple Myeloma, Hodgkin Lymphoma, Non-T, Non-B All Histiocytic Lymphoma, Non-Hodgkin Lymphoma (NHL) Burkitt Lymphoma, NHL follicular Lymphoma, Acute Myeloid Leukemia (AML), Anaplastic Large Cell Lymphoma (ALCL), Erythroleukemia, Colon Carinoma, Non-small Cell Lung Cancer (NSCLC), Small Cell Lung Cancer (SCLC), Renal Cell Caminoma (RCC), RCC clear cell type, RCC Papillary type, Melanoma, Pancreatic Carcinoma and Bladder Carcinoma. The following cells or cell lines were also used: Epstein-Barr virus-transformed B lymphoblastoid cell line (EBV-LCL), normal human mammary epithelial cells (HMEC), normal human vascular endothelial cells (HU-VEC), normal blood mononuclear (PBMC), normal human aortic endothelial cells (HAEC), normal human renal endothelial cells (HREC), normal human Lung Microvascular Endothelial Cells (HMVEC-L), normal human endo-neonatal dermal microvascular endothelial cells (HMVEC-neo) and normal human pulmonary artery endothelial cells (HPAEC).

Figure 2:
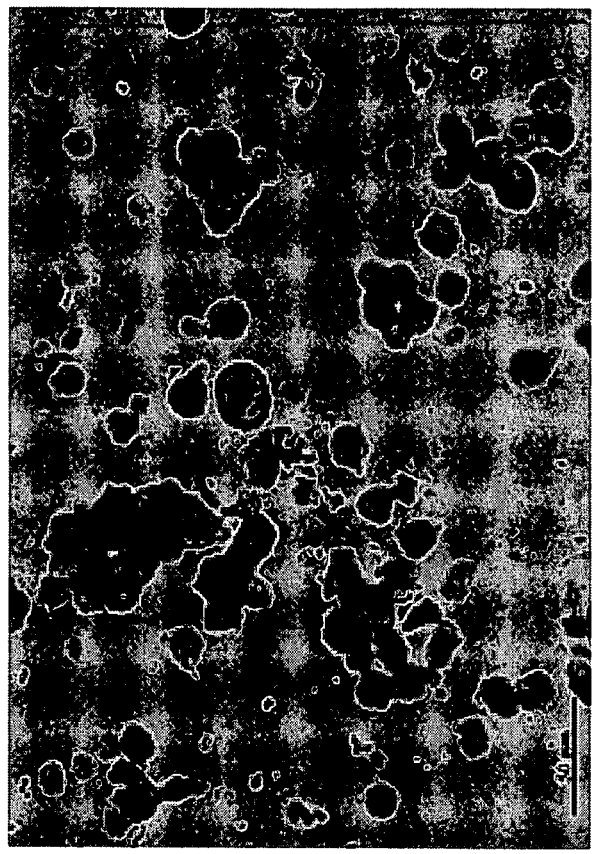
FIG. 2 shows CD70 protein expression on formalin fixed paraffin embedded (FFPE) pancreatic cell line PANC-1 using the SG21.1C1 antibody.
Figure 3:
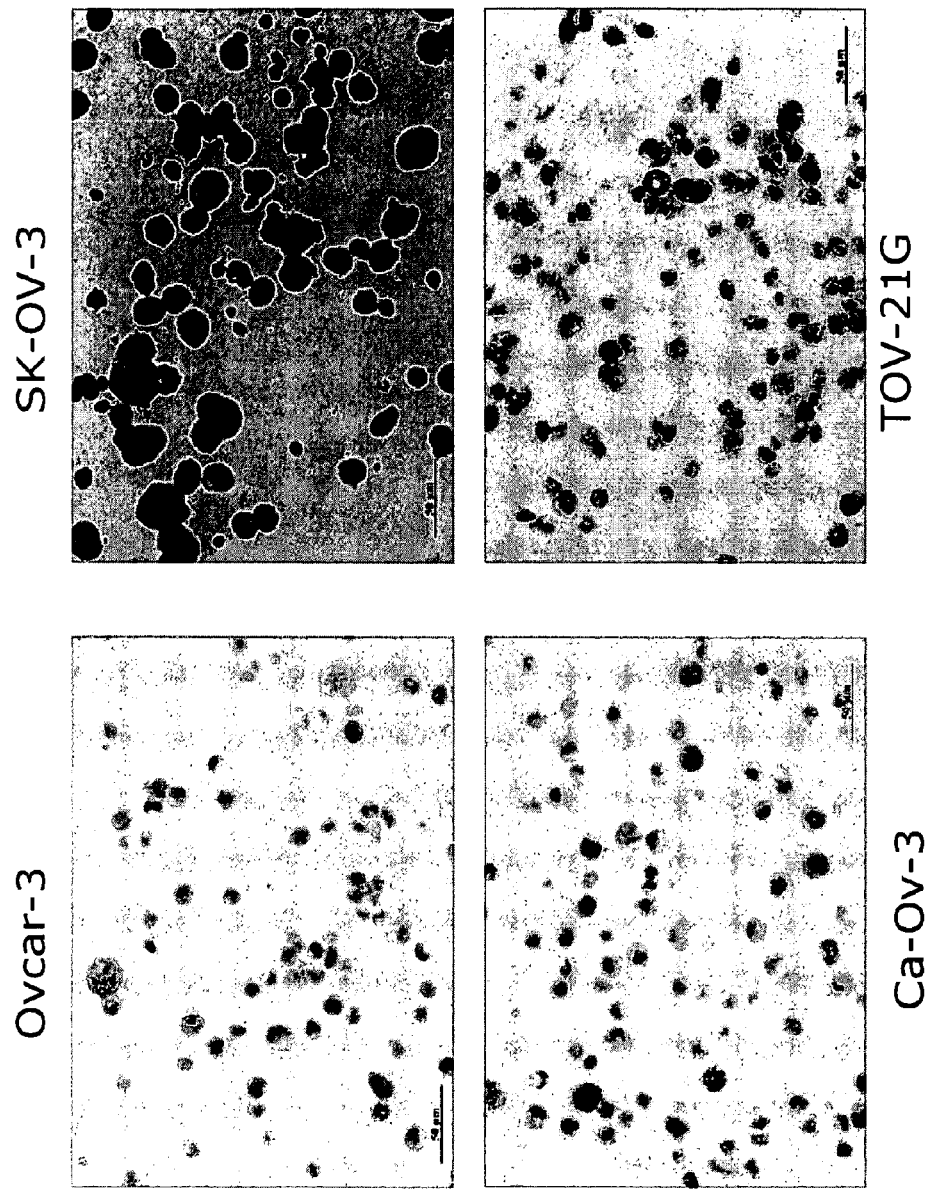
FIG. 3 shows CD70 protein expression in ovarian cell lines Ovcar-3, SK-OV-3, Ca-Ov-3 and TOV-21G using SG21.1C1 antibody.

The tissue microarrays were immuno-stained with SG21.1C1 antibodies using the protocol described above. Staining was observed in the following cell lines: Ovarian Carcinoma cell line SK-OV-3; Glioblastoma cell line GMS-10; Multiple Myeloma cell lines LB, LP-1, AMO-1, 1-310 (MM.1R), C2E3 (MM.1S), MOLP-8, JJN-3 and L363; Hodgkin lymphoma cell lines KMH2, HS445, RPMI-1666, L248 and HD-M-YZ; EBV-LCL WIL2-S, Farage and IM-9; NHL, follicular cell line WSU-NHL; RCC clear cell type cell lines Caki-1, Caki-2, 786-O and 769-P; RCC papillary type cell lines CAL54, A498; RCC SK-RC-6 and SK-RC-7; Melanoma cell lines A375M and A375SM, Pancreatic Carcinoma cell line PANC-1 and Bladder Carcinoma T24. The staining of some cell lines not identified was faint or mixed. Some cell lines have cytoplasmic staining. For the staining of pancreatic and ovarian cell lines, see FIGS. 2 and 3, respectively.

D. Comparative Staining of 1C1 and 5D12 Antibodies

1C1 and 5D12 antibodies were compared by staining 293F, 293F-cynoCF0 cell lines, RCC Caki-1, normal tonsil, skeletal muscle, bladder, lymphoid tissues (lymph node, thymus, spleen) from normal Cynomolgus monkeys, normal human thymus, kidney and skeletal muscle tissues and pancreatic tumor tissues. The immuno-staining protocol was as described above.

Figure 4:
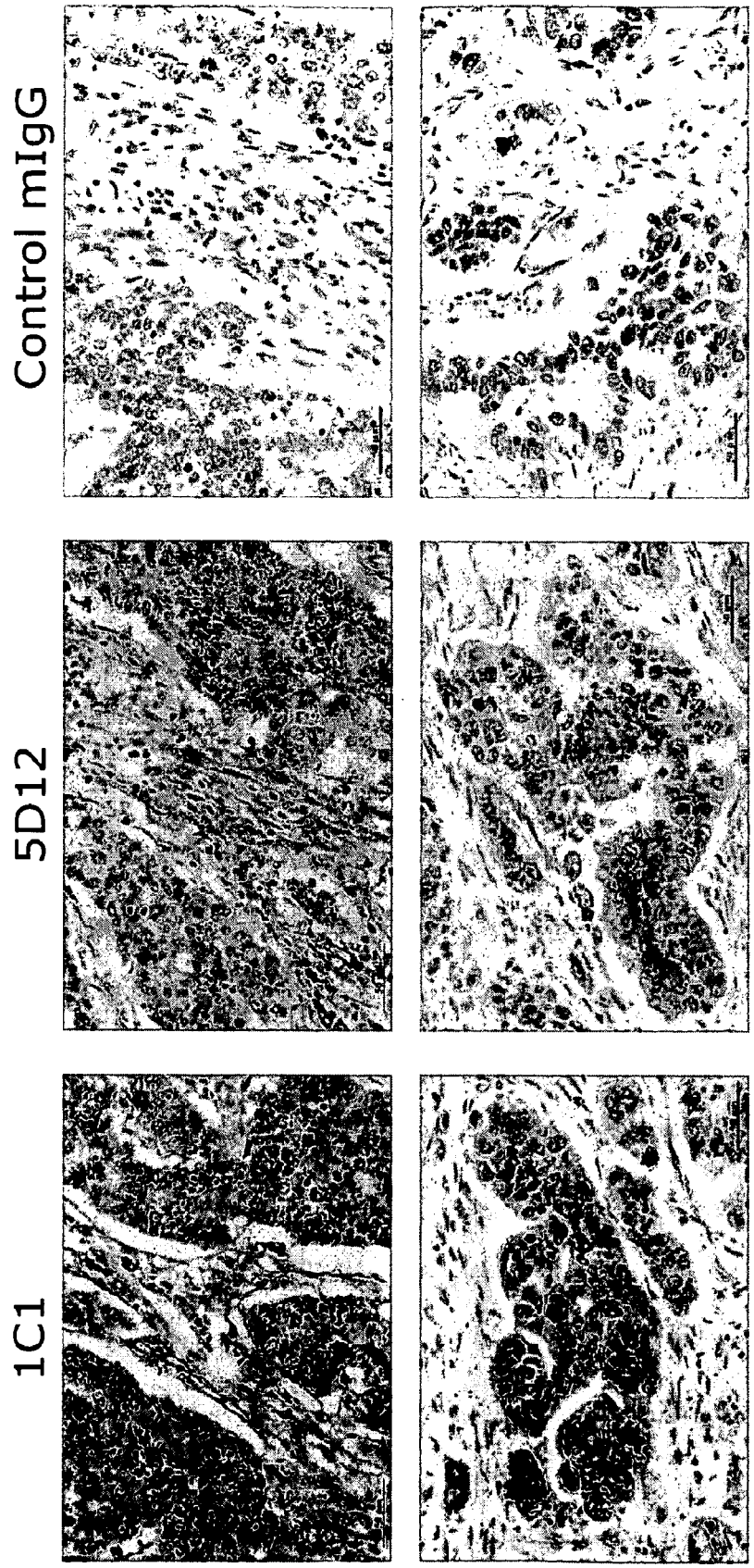
FIG. 4 shows CD70 protein expression in pancreatic tumor samples as detected by the antibodies SG-21.1C1 or SG-21.5D12 versus control mIgG.

The results showed that 1C1 and 5D12 similarly stained 293F and 293-cyno CD70 cell lines (data not shown); RCC Caki-1 and cynomolgus tonsil tissues (data not shown); lymphoid tissues (lymph node, thymus, spleen) from normal Cynomologous monkeys (data not shown) and pancreatic tumor tissues (see FIG. 4). Some differential staining of 1C1 and 5D12 was observed in normal human and monkey skeletal muscle tissues and normal monkey bladder tissues in which 5D12 stained the tissues but 1C1 did not. Differential staining was also observed in normal human thymus and kidney tissues in which 5D12 stained cytoplasmically.

Example 5

CD70 Expression in Normal Colon and Colorectal Cancer Tissues and Normal Pancreas and Pancreatic Cancer Tissues with 1C1 Antibody Before assessing the whole panel of tumor tissues from different cancer types, CD70 expression was first assayed in colon and pancreatic cancers. The immuno-staining protocol was as described in Example 4. The chromagen used for these studies was Fast Red.

Figure 5:
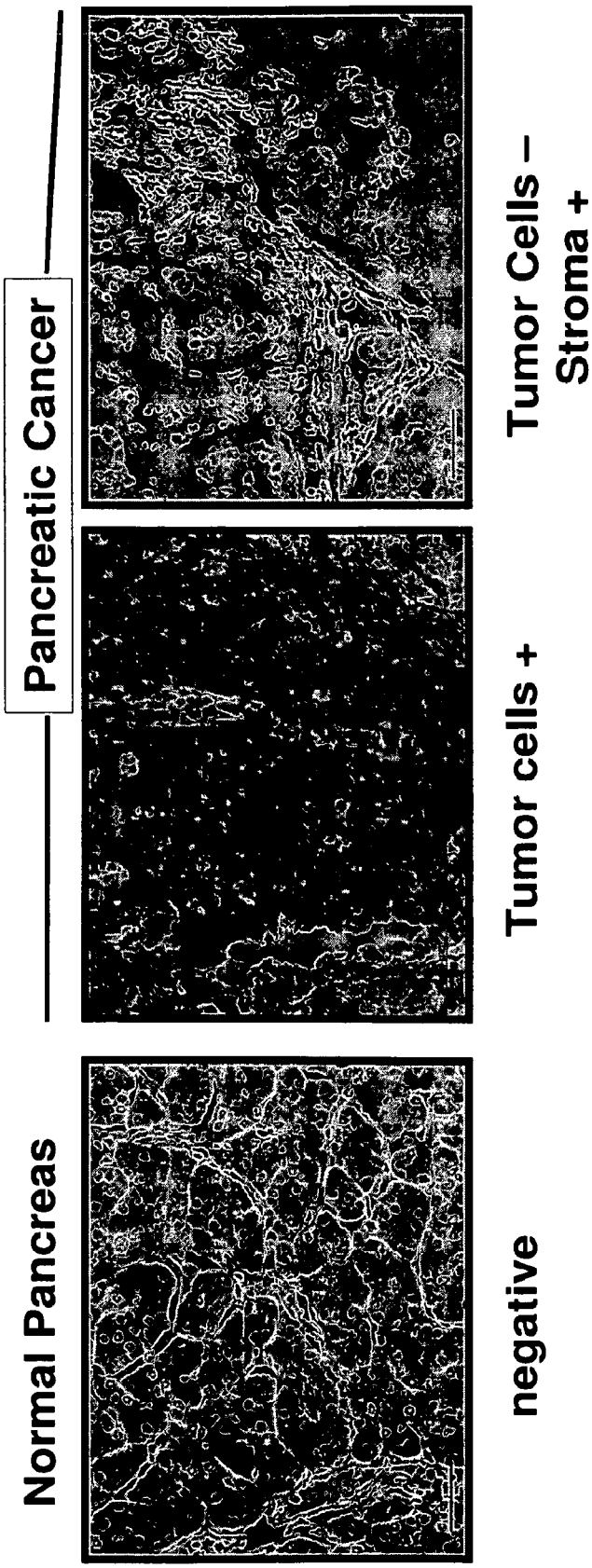
FIG. 5 shows CD70 protein expression on normal pancreatic and pancreatic tumor cells as detected by the SG-21.1C1 antibody using the chromogen Fast Red (darker color).

The results showed that in normal colon tissues, only rare lymphocytes were stained positive for CD70. Other cells were negative for CD70. In one sample of colon cancer tissue, the tumor cells were stained positive. In a second sample of colon tissue, the tumor cells were negative but the stroma was positive. Likewise, in normal pancreatic tissues, the staining was negative for CD70. In one sample of pancreatic cancer tissues, tumor cells were positive and in a second sample, tumor cells were negative but the stroma was positive. (See FIG. 5).

Example 6

CD70 Expression in Tumor Tissues with SG21.1C1 Antibody

Tumor tissues were obtained from the following tumor types: Hodgkin lymphoma, kidney, lymphoma, multiple myeloma, pancreas, larnyx/pharynx, ovary, colon and breast. The normal and tumor tissues were prepared according to the tissue array protocol described in Example 3 and the immuno-staining protocol was as described in Example 4A. 1C1 antibody was used as the primary antibody. The immunohistochemical (IHC) expression was later evaluated based on staining intensity and percentage of tumor involved. Staining intensity was ranked from 1 to 4, with 1 indicating minimal staining; 2, mild staining; 3, moderate staining and 4, strong staining. Percentage of tumor involved was also ranked from 1 to 4, with 1 indicating 0-5%; 2, 5-25%; 3, 25-75% and 4, 75%-100%. The measurements were qualitative. For Hodgkin lymphoma, IHC expression of CD70-positive cells was assayed based on Reed-Sternberg cell evaluation. Reed-Sternberg cells are large cells of unknown origin, usually multinucleate, whose presence is the common histological characteristic of Hodgkin lymphoma.

Hodgkin lymphoma tumor tissues had the highest percentage (97% or 33/34) of CF70-positive tumor cells over cells in the total tumors. Kidney tumor had the second highest percentage (70% or 14/20) of CF70-positive tumor cells over cells in the total tumors. Lymphoma had the third highest percentage (61% or 72/119) of CD70-positive tumor cells over cells in the total tumors. Multiple Myeloma had the fourth highest percentage (42% or 13/31) of CF70-positive tumor cells over cells in the total tumors. Pancreas cancer had the fifth highest percentage (25% or 35/140) of CF70-positive tumor cells over cells in the total tumors.

Figure 6:
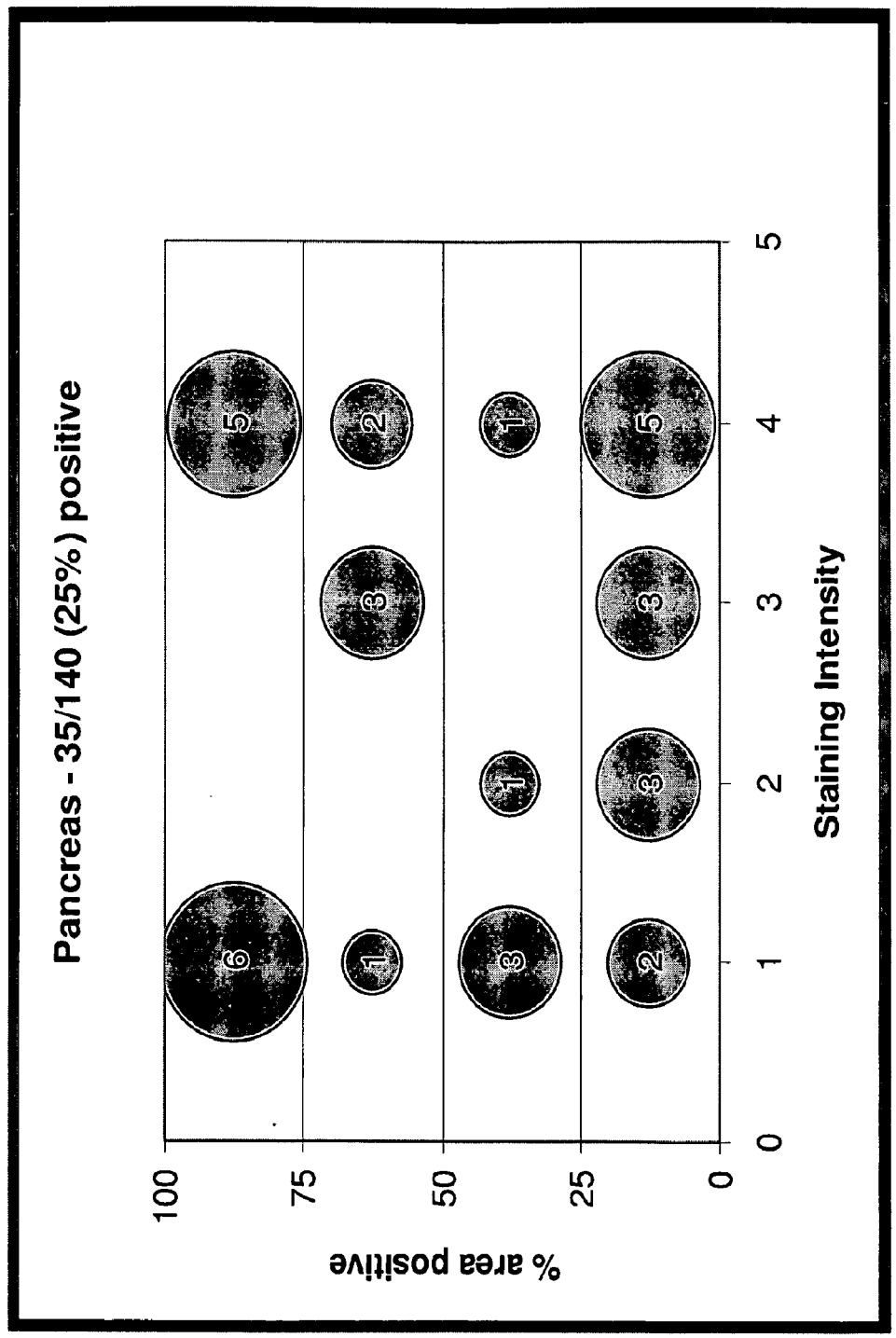
FIG. 6 shows an evaluation of CD70 protein expression in pancreatic cancer cells. The x-axis indicates the CD70 staining intensity and the y-axis indicates the percentage of the area that is CD70-positive.

FIG. 6 illustrates a graph of staining intensity and % of tumor staining for 35 of 140 pancreatic samples giving a positive signal for CD70. The figure shows a complex relationship between the staining intensity and percentage of tumor staining. That is, some tumors have a high percentage of cells staining but at low intensity, others have a low percentage of cells staining but at high intensity, and others show intermediate staining intensity and percentage cells staining. Larnyx/pharnyx cancer had the sixth highest percentage (22% or 18/82) of CF70 positive-tumor cells over cells in the total tumors. Ovarian Cancer had the seventh highest percentage (15% or 37/241) of CF70-positive tumor cells over cells in the total tumors.

Figure 7:
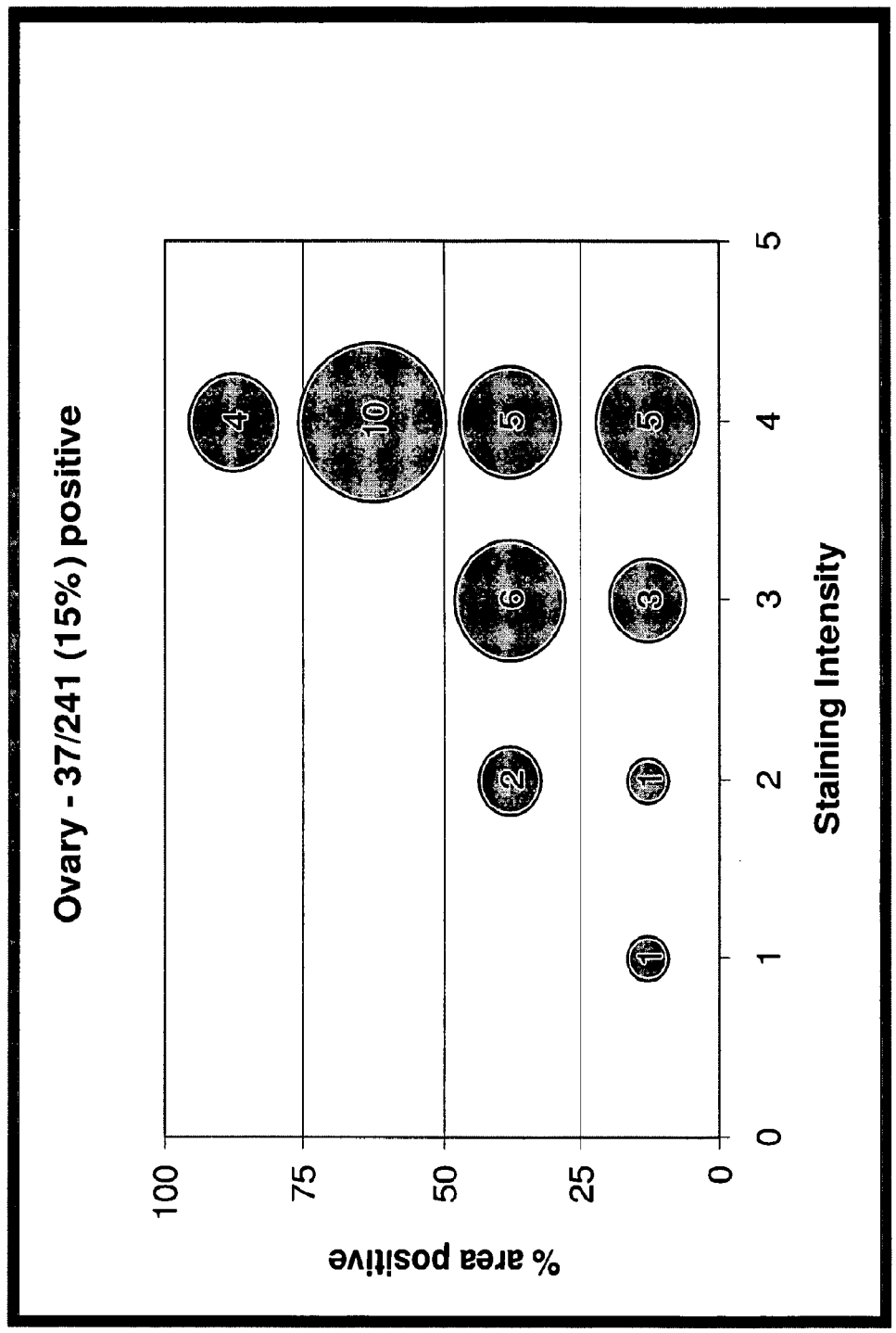
FIG. 7 shows an evaluation of CD70 protein expression in ovarian tumors. The x-axis indicates the CD70 staining intensity and the y-axis indicates the percentage of area that is CD70-positive.

FIG. 7 illustrates staining intensity and percent of tumor staining for 37 of 241 CD70 staining ovarian cancers. There was some association between staining intensity and percentage of cells staining. Colorectal Cancer had the seventh highest percentage (9% or 17/194) of CF70-positive tumor cells over cells in the total tumors. Breast Cancer had the lowest percentage (2% or 5/204) of CF70-positive tumor cells over cells in the total tumors.

To summarize, based on CD70-positive tumors/total tumors, stain intensity (cellular target expression), percentage of CD70-positive tumor involvement (tumor target expression), general indication ranking of the tumor types is as follows: Hodgkin>Kidney>Lymphoma>Multiple Myeloma>Pancreatic>Larnyx/pharnyx>Ovarian>Colorectal>Breast. The results of all the tumor tissues are shown on Table 1.

TABLE 1

CD70 Expression in Various Cancers

| Tumor Type | CD70+/Total | % of CD70+ |
|---|---|---|
| Hodgkin | 33/34 | 97 |
| Kidney | 204/283 | 72 |

TABLE 1-continued

CD70 Expression in Various Cancers

| Tumor Type | CD70+/ Total | % of CD70+ |
| --- | --- | --- |
| Lymphoma | 72/119 | 61 |
| Multiple Myeloma | 13/31 | 42 |
| Pancreas | 35/140 | 25 |
| Larnyx/ Pharynx | 18/82 | 22 |
| Ovary | 37/241 | 15 |
| Skin | 4/30 | 13 |
| Lung (all) | 40/475 | 8 |
| Lung adenocarcinoma | 17/172 | 10 |
| Colon | 17/194 | 9 |
| Breast | 5/204 | 2 |

Example 7 h1F6-Drug Conjugates Show Efficacy in an Ovarian Carcinoma Cell Line

To confirm the efficacy of known anti-CD70 antibody drug conjugates against representative cell lines for these new cancers, SKOV-3 cells were prepared and tested as generally described previously for other cell lines. (See International Patent Publication WO 2006-113909.) The cells were incubated with the following anti-CD70 antibody drug conjugates: h1F6-vc-MMAF(4), h1F6vc-MMAE(4), 1F6mc-MMAF(4), or h1F6mc-MMAF(8) or free MMAF. (See the specification and U.S. Patent Application Publication Nos. 2005-0238649 and 2006-0233794 for a description of the drug linkers. The number in parentheses after each conjugate indicates the average drug loading per antibody.) The SKOV-3 cells were incubated with the conjugates at the indicated concentrations for 96 hours. For these studies, viability was determined using Promega CelltiterGlo.

TABLE 2

| h1F6vc-MMAF(4) | h1F6vc-MMAE(4) | h1F6mc-MMAF(4) | h1F6mc-MMAF(8) | MMAF |
| --- | --- | --- | --- | --- |
| 5 ng/ml | 60 ng/ml | 29 ng/ml | 12 ng/ml | 18 nM |

Figure 8:
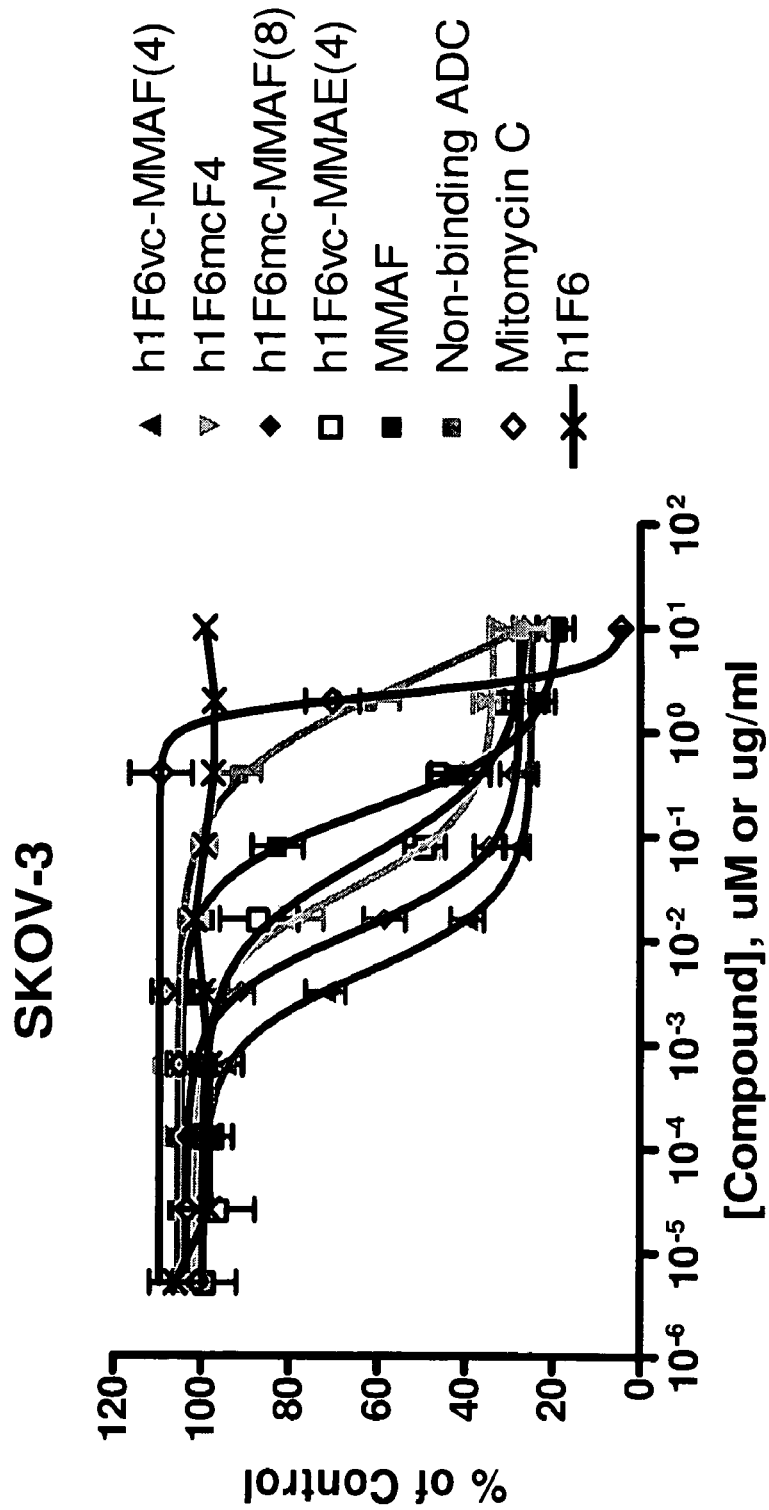
FIG. 8 shows an evaluation of the in vitro cytotoxic activity of various a humanized 1F6 antibody drug conjugates against an ovarian cancer cell line, SKOV-3.

Referring to FIG. 8, all four anti-CD70 ADCs were active against this ovarian cancer cell line. Referring to Table 2, the IC50's are shown. These IC50's are consistent with those reported for other CD70-expressing cancer cell lines. These results confirm that anti-CD70 ADCs bound to CD70 on this cancer cell line is internalized and releases the auristatin payload.

Figure 9:
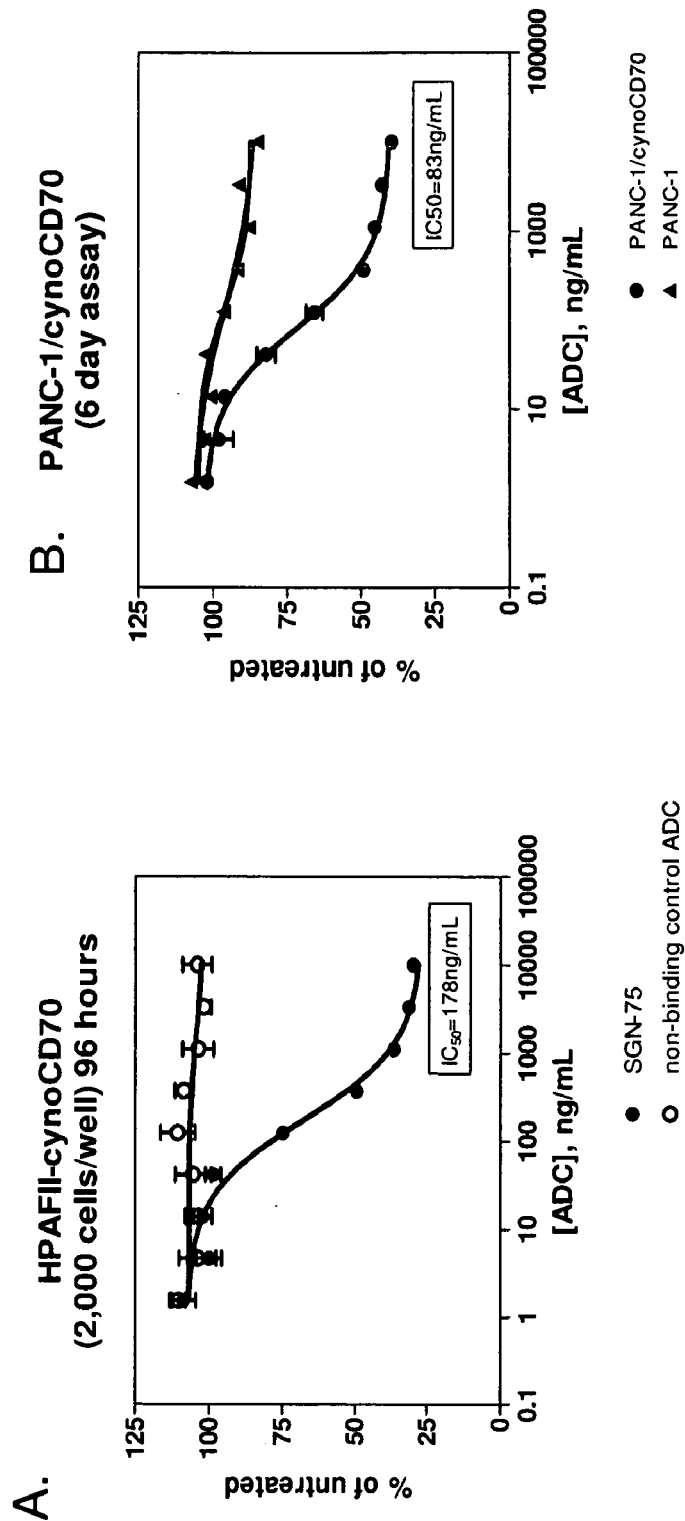
FIGS. 9A-C show evaluations of the in vitro cytotoxic activity of a humanized 1F6 antibody drug conjugate on the following cell lines: (A) a CD70-transfected pancreatic cell line, HPAFII; (B) a CD70 transfected PANC-1 pancreatic cell line; and (C) a CD70 transfected MiaPaCa-2 cell line.
Figure 9:
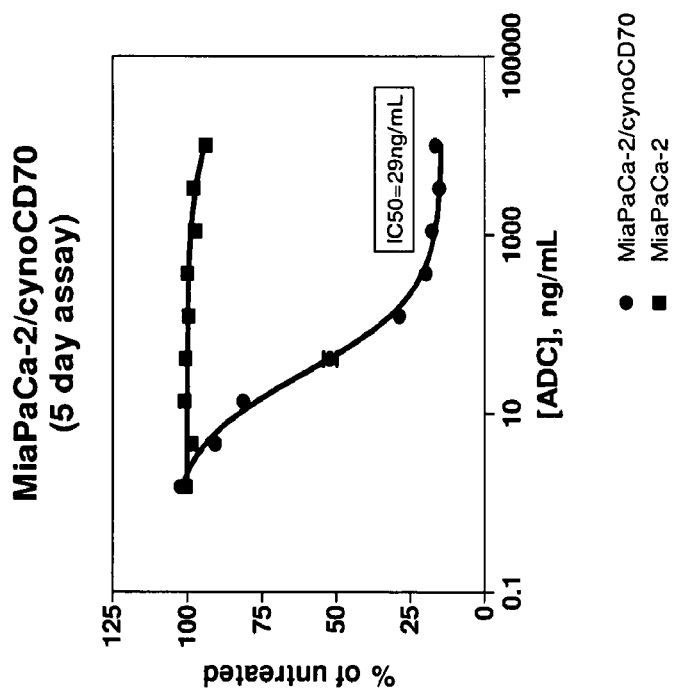

Example 8 h1F6-Drug Conjugates Show Efficacy in a CD70 Transfected Pancreatic Carcinoma Cell Line To confirm the efficacy of known anti-CD70 antibody drug conjugates against representative cell lines, the pancreatic cell lines HPAFII, PANC-1 and MiaPaCa-2 were transfected with a modified cynomolgus CD70 encoding nucleic acid. MiaPaCa-2 cells do not express detectable levels of CD70 protein. h1F6 binds to native CD70 protein expressed by these transfected cell lines. The expression of CD70 by the transfected cell lines was confirmed by FACS analysis (data not shown). The activity of h1F6 mc-MMAF(4) (SGN-75) was tested on the transfected pancreatic cell lines generally described previously for other cell lines. (See Example 7 an International Patent Publication WO 2006-113909.) (The number in parentheses after the conjugate indicates the average drug loading per antibody.) Referring to FIGS. 9A-C, the cells were incubated with the conjugate at the indicated concentrations for 96 hours. Referring to FIG. 9A, the activity of the conjugate on the transfected HPAFII cells is shown. Cell viability was determined using Promega CelltiterGlo. Referring to FIGS. 9B and 9C, the activity of the conjugate on transfected PANC-1 and MiaPACa-2 transfected cell lines is shown. For these studies, cell viability was determined using rezasurin, as described previously. The PANC-1 Activity of Promega CelltiterGlo. The conjugate showed cytotoxic activity on all these cell lines in vitro.

Example 9 h1F6-Drug Conjugates Show Efficacy in a Xenograft Model of Pancreatic Cancer

Figure 10:
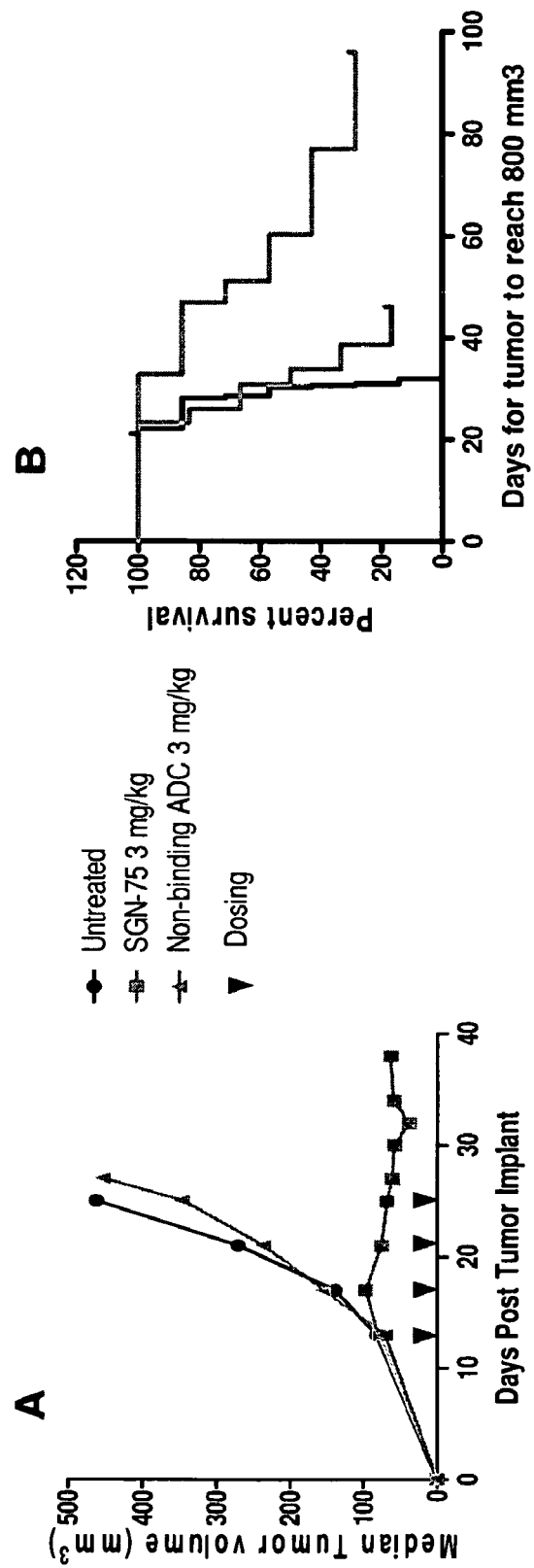
FIG. 10 shows an evaluation of the in vivo efficacy of a humanized 1F6 antibody drug conjugate on CD70-transfected MiaPaCa pancreatic carcinoma tumors in nude mice.

Nude (nu/nu) female mice (7 animals/group) were implanted with CD70-transfected MiaPaCa tumor chunks (prepared as described in Example 8) via trocar into the right lateral flank. Dosing with either SGN-75 or nonbinding control ADC (3 mg/kg) started when tumors reached 100 mm³ (q4d×4 ip). Tumor volumes were monitored and animals were euthanized when tumor volume reached 1000 mm³. Referring to FIG. 10, the data were plotted in 2 ways: A. Median tumor volume plots were continued for each group until one or more animals were euthanized. B. Kaplan-Meier curve shows time for tumor to reach 800 mm³ for individual animals in each group. Treatment with SGN-75 was effective in this xenograft model.

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

What is claimed is:

1. A monoclonal antibody that specifically binds to denatured human CD70 on a sample of formalin fixed, paraffin-embedded cells or tissues that express human CD70, wherein the monoclonal antibody comprises three heavy chain complementarity determining regions (CDRs): heavy chain CDR1, heavy chain CDR2, and heavy chain CDR3, wherein the heavy chain CDRs are identical to the heavy chain CDRs of the antibody SG-21.1C1; and three light chain CDRs: light chain CDR1, light chain CDR2, and light chain CDR3, wherein the light chain CDRs are identical to the light chain CDRs of the antibody SG-21.1C, and wherein the antibody SG-21.1C is produced by the hybridoma deposited with the ATCC and assigned Accession No. PTA-8733.

2. The monoclonal antibody of claim 1, which is a chimeric or humanized antibody.

3. The monoclonal antibody of claim 1, that is antibody SG-21.1C1 as produced by the hybridoma deposited with the ATCC and assigned Accession No. PTA-8733.

4. The monoclonal antibody of claim 1, comprising the heavy chain variable region of the antibody SG-21.1C1 and light chain variable region of the antibody SG-21.1C1.

5. A diagnostic kit, comprising: the monoclonal antibody of claim 1.

6. A method of detecting expression of CD70 in a tissue sample of a patient, comprising
  obtaining a tissue sample of pancreas, ovary, lung, larynx, pharynx, breast, or skin from the patient;
  fixing the tissue sample and denaturing CD70 in the tissue sample, wherein the sample is fixed in formalin and embedded in paraffin;
  contacting the fixed tissue sample with the monoclonal antibody of claim 1; and detecting binding of the monoclonal antibody to the fixed tissue sample to determine whether CD70 is expressed in the sample.

7. A combination diagnostic and pharmaceutical kit comprising the monoclonal antibody of claim 1 for use in diagnosis and an antibody that specifically binds to an extracellular domain of native of CD70 for use in therapy.

8. The monoclonal antibody of claim 1, wherein the antibody binds to the extracellular domain of human CD70 protein.

9. The monoclonal antibody of claim 1, wherein the antibody cross-reacts with a cynomolgous CD70 protein.

* * * * *